United States Patent
Driehuys et al.

(10) Patent No.: US 6,199,385 B1
(45) Date of Patent: Mar. 13, 2001

(54) POLARIZED GAS ACCUMULATORS AND HEATING JACKETS AND ASSOCIATED GAS COLLECTION AND THAW METHODS AND POLARIZED GAS PRODUCTS

(75) Inventors: Bastiaan Driehuys, Durham; David Zollinger, Chapel Hill; Daniel Deaton, Raleigh; K. C. Hasson, Durham, all of NC (US); Alan Langhorn, Encinitas, CA (US)

(73) Assignee: Medi-Physics, Inc., Princeton, NJ (US)

( * ) Notice: Subject to any disclaimer, the term of this patent is extended or adjusted under 35 U.S.C. 154(b) by 0 days.

(21) Appl. No.: 09/210,020

(22) Filed: Dec. 11, 1998

Related U.S. Application Data

(60) Provisional application No. 60/069,435, filed on Dec. 12, 1997.

(51) Int. Cl.$^7$ .................................................. F25B 19/00
(52) U.S. Cl. .............................. 62/51.1; 62/919; 62/925
(58) Field of Search .............................. 62/51.1, 919, 925

(56) References Cited

U.S. PATENT DOCUMENTS

| | | | |
|---|---|---|---|
| 3,487,651 | * | 1/1970 | Schleich et al. ...................... 62/919 |
| 3,748,864 | | 7/1973 | Lofredo et al. ........................ 62/22 |
| 4,080,429 | | 3/1978 | Koeppe et al. ...................... 423/262 |

(List continued on next page.)

FOREIGN PATENT DOCUMENTS

| | | |
|---|---|---|
| PCT/US97/05004 | 3/1997 | (WO) . |
| PCT/US97/05084 | 3/1997 | (WO) . |
| PCT/US97/05166 | 3/1997 | (WO) . |

OTHER PUBLICATIONS

Abstract, Breathe (xenon) deeply to see lungs clearly; inert gas xenon may make magnetic resonance imaging more effective in visualizing brain and lungs tissues, PROMT—Predicasts: PM1.

Albert et al., "$^{129}$Xe Relaxation Catalysis by Oxygen", Abstracts of the 11th Annual Meetings of the Society for Magnetic Resonance Medicine, (1992).

Albert et al., "Relaxation of $^{129}$Xe in Model Biological Systems: On Probing the mechanism of General Anesthesia", Abstracts of the 11th Annual Meetings of the Society for Magnetic Resonance Medicine, (1992).

Albert, "Measurement of $^{129}$Xe T1 in blood to explore the feasibility of hyperpolarized sup 129Xe MRI," Jour. Comp. Ass. Tomography, vol. 19, No. 6 (Nov.–Dec. 1995).

Becker et al., "Study Of Mechanical Compression Of Spin–Polarized $^3$He Gas", *Nuclear Instruments And Methods In Physics Research*, vol. A 346, pp. 45–51 (1994).

Bhasker et al., "Efficiency of Spin Exchange between Rubidium Spins and $^{129}$Xe Nuclei in a Gas", *Physical Review Letters*, vol. 49, p. 25 (1982).

Borman, Xenon used to expand magnetic imaging, Chem. & Eng. News, vol. News, vol. 72, No. 30, pp. 7–8 (Jul. 25, 1994).

(List continued on next page.)

Primary Examiner—Ronald Capossela
(74) Attorney, Agent, or Firm—Myers Bigel Sibley & Sajovec, P.A.

(57) ABSTRACT

Methods of collecting, thawing, and extending the useful polarized life of frozen polarized gases include heating a portion of the flow path and/or directly liquefying the frozen gas during thawing. A polarized noble gas product with an extended polarized life product is also included. Associated apparatus such as an accumulator and heating jacket for collecting, storing, and transporting polarized noble gases include a secondary flow channel which provides heat to a portion of the collection path during accumulation and during thawing.

44 Claims, 13 Drawing Sheets

U.S. PATENT DOCUMENTS

| | | | |
|---|---|---|---|
| 4,369,048 | | 1/1983 | Pence ........................................ 55/66 |
| 4,417,909 | | 11/1983 | Weltmer, Jr. ............................. 62/12 |
| 4,586,511 | | 5/1986 | Clark, Jr. ............................. 128/653 |
| 4,599,462 | | 7/1986 | Michl .................................. 568/702 |
| 4,666,480 | * | 5/1987 | Mann .................................... 62/919 |
| 4,755,201 | | 7/1988 | Eschwey .................................. 62/12 |
| 4,756,167 | * | 7/1988 | Kuriyama et al. .................... 62/51.1 |
| 4,977,749 | | 12/1990 | Sercel ................................... 62/51.1 |
| 5,007,243 | | 4/1991 | Yamaguchi et al. .................. 62/51.1 |
| 5,039,500 | | 8/1991 | Shino et al. ......................... 423/262 |
| 5,161,382 | | 11/1992 | Missimer ............................. 62/46.1 |
| 5,545,396 | | 8/1996 | Albert et al. ........................... 424/93 |
| 5,612,103 | | 3/1997 | Driehuys et al. ................... 428/34.7 |
| 5,617,860 | | 4/1997 | Chupp et al. ...................... 128/653.4 |
| 5,642,625 | | 7/1997 | Cates, Jr. et al. ..................... 62/55.5 |
| 5,809,801 | | 9/1998 | Cates, Jr. et al. ....................... 62/637 |
| 5,934,103 | | 8/1999 | Ryan et al. ............................ 62/637 |

OTHER PUBLICATIONS

Cates et al., "Laser Production of Large Nuclear–Spin Polarization in Frozen Xenon", *Phys. Rev. Lett.*, vol. 65, No. 20, pp. 2591–2594 (1990).

Cates et al., "Rb–$^{129}$Xe spin–exchange rates due to binary and three–body collisions at High Xe pressures", *Physical Review A*, vol. 45, p. 4631 (1992).

Cummings et al., "Optical pumping of Rb vapor using high–power $Ga_{1-x}A_x$ As diode laser arrays", *Phys. Rev. A*, vol. 51, No. 6, pp. 4842–4851 (1995).

Driehuys et al., "High–volume production of laser–polarized $^{129}$Xe", *Appl. Phys. Lett.*, vol. 69, No. 12 (1996).

Gatzke et al., "Extraordinarily Slow Nuclear Spin Relaxation in Frozen Lazer–Polarized $^{129}$Xe", *Phys. Rev. Lett.*, vol. 70, No. 5, pp. 690–693 (1993).

George, "The sharper image: MRIs and xenon gas," Jour. of NIH Res., vol. 6, No. 12, pp. 42–44 (Dec. 1994).

Kaatz, "Comparison of molecular hyperpolarizabilities from gas and liquid," Jour. Chemical Physics, vol. 108, No. 3, pp. 849–856 (Jan. 15, 1998).

Martin, "The pharmacokinetics of hyperpolarized xenon: implications for cerebral MRI," Jour. Magn. Reson. Imag., vol. 7, No. 5, pp. 848–854 (Sep.–Oct 1997).

Middleton et al., "MR Imaging With Hyperpolarized $^3$He Gas", *Magnetic Resonance In Medicine*, vol. 33, pp. 271–275 (1995).

Middleton, "The Spin Structure of The Neutron Determined Using A Polarized $^3$He Target", *Ph. D. Dissertation*, Princeton University (1994).

Miller et al., "Xenon NMR: Chemical shifts of a general anesthetic common solvents, proteins, and membranes", *Proc. of the Nat. Academy of Science (USA)*, vol. 78, No. 8 (1981).

Mugler, "MR imaging and spectroscopy using hyperpolarized 129Xe gas: preliminary human results," Mag. Reson. Med., vol. 37, No. 6, pp. 809–815 (Jun. 1997).

Patyal, "Longitudinal relaxation and diffusion measurements using magnetic resonance signals from laser–hyperpolarized 129Xe nuclei," J. Magn. Reson., vol. 126, No. 1, pp. 58–65, May 1997.

Raftery, D. et al., "NMR of optically pumped xenon this films", *Chem. Phys. Lett.*, vol. 191, pp. 385–390 (1992).

Sauer et al., "Laser Polarized Liquid Xenon", *Chem. Phys. Lett.*, vol. 277, pp. 153–158 (1977).

Wagshul, "In vivo MR imaging and spectroscopy using hyperpolarized 129Xe," Magn. Reson. Med., vol. 36, No. 2, pp. 183–191 (Aug. 1996).

Wilson, E.K., Hyperpolarized Gases Set NMR World Spinning, Chem. & Eng. News, vol. 74, No. 52, pp. 21–24 (Dec. 23, 1996).

Zeng et al., "Experimental determination of the rate constants for spin sxchange between optically pumped K, Rb, and Cs atoms and $^{129}$Xe nuclei in alkali–metal—noble–gas van der Waals molecules", *Physical Review A*, vol. 31, p. 260 (1985).

* cited by examiner

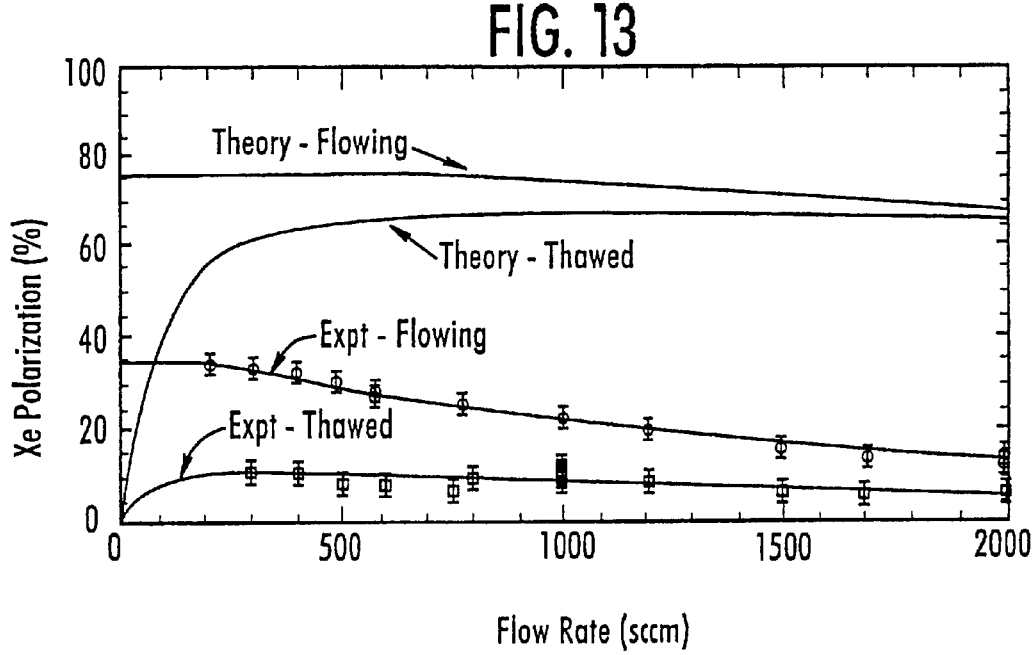
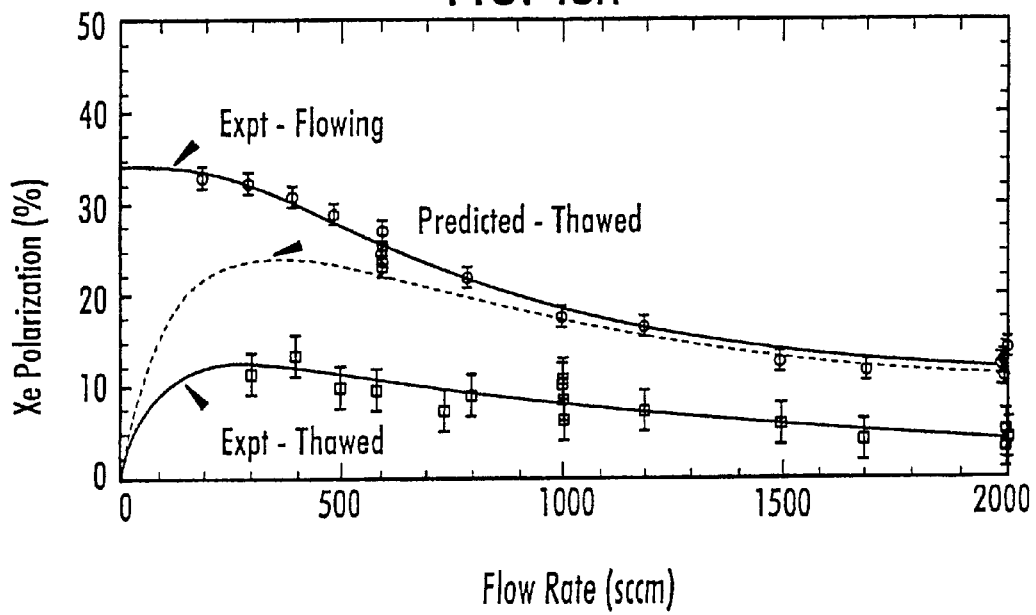

POLARIZED GAS ACCUMULATORS AND HEATING JACKETS AND ASSOCIATED GAS COLLECTION AND THAW METHODS AND POLARIZED GAS PRODUCTS

This appln claims the benefit of U.S. Provisional Ser. No. 60/069,435 filed Dec. 12, 1997.

This invention was made with Government support under AFSOR Grant number F41624-97-C-9001. The United States Government has certain rights in this invention.

FIELD OF THE INVENTION

The present invention relates to the collection and accumulation of polarized noble gases, and relates more particularly to the production of hyperpolarized gases for use in medical diagnostic procedures such as magnetic resonance imaging ("MRI") and spectroscopy applications.

BACKGROUND OF THE INVENTION

Conventionally, MRI has been used to produce images by exciting the nuclei of hydrogen molecules (present in water protons) in the human body. However, it has recently been discovered that polarized noble gases can produce improved images of certain areas and regions of the body which have heretofore produced less than satisfactory images in this modality. Polarized Helium 3 ("$^3$He") and Xenon-129 ("$^{129}$Xe") have been found to be particularly suited for this purpose. Unfortunately, as will be discussed further below, the polarized state of the gases is sensitive to handling and environmental conditions and can, undesirably, decay from the polarized state relatively quickly.

Hyperpolarizers are used to produce and accumulate polarized noble gases. Hyperpolarizers artificially enhance the polarization of certain noble gas nuclei (such as $^{129}$Xe or $^3$He) over the natural or equilibrium levels, i.e., the Boltzmann polarization. Such an increase is desirable because it enhances and increases the Magnetic Resonance Imaging ("MRI") signal intensity, allowing physicians to obtain better images of the substance in the body. See U.S. Pat. No. 5,545,396 to Albert et al., the disclosure of which is hereby incorporated herein by reference as if recited in full herein.

In order to produce the hyperpolarized gas, the noble gas is typically blended with optically pumped alkali metal vapors such as rubidium ("Rb"). These optically pumped metal vapors collide with the nuclei of the noble gas and hyperpolarize the noble gas through a phenomenon known as "spin-exchange". The "optical pumping" of the alkali metal vapor is produced by irradiating the alkali-metal vapor with circularly polarized light at the wavelength of the first principal resonance for the alkali metal (e.g., 795 nm for Rb). Generally stated, the ground state atoms become excited, then subsequently decay back to the ground state. Under a modest magnetic field (10 Gauss), the cycling of atoms between the ground and excited states can yield nearly 100% polarization of the atoms in a few microseconds. This polarization is generally carried by the lone valence electron characteristics of the alkali metal. In the presence of non-zero nuclear spin noble gases, the alkali-metal vapor atoms can collide with the noble gas atoms in a manner in which the polarization of the valence electrons is transferred to the noble-gas nuclei through a mutual spin flip "spin-exchange".

Conventionally, lasers have been used to optically pump the alkali metals. Various lasers emit light signals over various wavelength bands. In order to improve the optical pumping process for certain types of lasers (particularly those with broader bandwidth emissions), the absorption or resonance line width of the alkali metal can be made broader to more closely correspond with the particular laser emission bandwidth of the selected laser. This broadening can be achieved by pressure broadening, i.e., by using a buffer gas in the optical pumping chamber. Collisions of the alkali metal vapor with a buffer gas will lead to a broadening of the alkali's absorption bandwidth.

For example, it is known that the amount of polarized $^{129}$Xe which can be produced per unit time is directly proportional to the light power absorbed by the Rb vapor. Thus, polarizing $^{129}$Xe in large quantities generally takes a large amount of laser power. When using a diode laser array, the natural Rb absorption line bandwidth is typically many times narrower than the laser emission bandwidth. The Rb absorption range can be increased by using a buffer gas. Of course, the selection of a buffer gas can also undesirably impact the Rb-noble gas spin-exchange by potentially introducing an angular momentum loss of the alkali metal to the buffer gas rather than to the noble gas as desired.

In any event, after the spin-exchange has been completed, the hyperpolarized gas is separated from the alkali metal prior to introduction into a patient. Unfortunately, after and during collection, the hyperpolarized gas can deteriorate or decay relatively quickly (lose its hyperpolarized state) and therefore must be handled, collected, transported, and stored carefully. Thus, handling of the hyperpolarized gases is critical, because of the sensitivity of the hyperpolarized state to environmental and handling factors and the potential for undesirable decay of the gas from its hyperpolarized state.

Some accumulation systems employ cryogenic accumulators to separate the buffer gas from the polarized gas and to freeze the collected polarized gas. Unfortunately, reductions in polarization of the gas can be problematic as, after final thawing of the frozen gas, the polarization level of the gas can potentially be undesirably reduced by as much as an order of magnitude. Further and disadvantageously, the extremely low operating temperatures of the accumulator near the cryogen source can sometimes clog the collection area of the accumulator, thereby decreasing the rate of, or even preventing, further collection.

OBJECTS AND SUMMARY OF THE INVENTION

In view of the foregoing, it is therefore an object of the present invention to extend the polarization life of collected polarized noble gases and to reduce the amount of de-polarization in the collected polarized gas prior to the end use point.

It is another object of the present invention to provide an improved cryogenic accumulator which can be used in a substantially continuous production environment.

It is a further object of the present invention to provide an improved collection device and method which reduces the amount of polarization lost during processing.

It is yet another object of the invention to provide a method which will minimize the de-polarization effects attributed to thawing a frozen polarized gas product prior to delivery to an end user.

These and other objects are satisfied by the present invention by a cryogenic accumulator with an internal heating jacket. In particular, a first aspect of the invention is directed to a cryogenic accumulator for collecting polarized noble gases which includes a primary flow channel having opposing first and second ends configured to direct polarized gas therethrough, and an outer sleeve positioned around the primary flow channel. The outer sleeve has a closed end defining a collection chamber positioned below the flow channel second end. The accumulator also includes a secondary flow channel positioned intermediate of the primary flow channel and the outer sleeve. The secondary flow channel has a closed end positioned in close proximity to the primary flow channel second end.

In a preferred embodiment, the outer sleeve and the outer wall of the secondary flow channel define a buffer gas exit channel therebetween and the (circumferentially extending) inner wall of the secondary flow channel defines the primary flow channel. It is also preferred that the primary flow channel second end be configured as a nozzle and that the secondary flow channel be configured as a warming or heating jacket to direct circulating room temperature dry gases such as nitrogen therethrough. The circulating nitrogen is separate from the flow channel and acts to compensate or protect the nozzle area against the cold buffer gas exiting along the outside of the primary flow channel and the cryogenic temperatures associated with the cryogen bath. Advantageously, such a secondary flow channel can reduce the likelihood that the primary flow nozzle will freeze and clog from sublimation of the noble gas.

Further and preferably, the accumulator includes first and second isolation valves in communication with the primary flow channel and the buffer gas exit channel. The first isolation valve is positioned at the first end of the primary flow channel and can be used to control the flow of a target gas therethrough. The second isolation valve is positioned spaced-apart from the outer sleeve closed end along the buffer gas exit channel to releasably seal and control the release of buffer gas therethrough. In this embodiment, the accumulator is configured to contain MRI-sized quantities (such as 0.5–2 liters of polarized gas) and is detachably releasable from a hyperpolarizer unit for easy transport to a remote site.

Another aspect of the present invention relates to a heating jacket for a refrigerated accumulator. The jacket includes an outer wall having opposing first and second ends and an inner wall having opposing first and second ends. The inner wall is spaced apart from the outer wall. The inner wall is configured to be in close proximity to a polarized gas collection path. The jacket also includes a top and bottom which bridge and seal each of the outer and inner walls. The top, bottom and outer and inner walls define at least one enclosed fluid (such as a gas or liquid) circulation channel therebetween. The jacket also includes a fluid and a fluid vent, each of which is in communication with the circulation channel. The fluid inlet and vent are configured to allow flow of a fluid, gas, or gas mixture in the circulation channel.

In a preferred embodiment, the heating jacket fluid inlet is operably associated with a valve such that it is configured to provide a predetermined flow rate of the gas in the circulation channel. It is also preferred that the inner wall circumferentially extends around a center opening to define a flow channel therethrough for a polarized gas.

It is additionally preferred that the inner wall include a first portion which defines a flow channel first diameter and a stepped down portion which defines a flow channel second diameter. In this embodiment, the second diameter is smaller than the first diameter and defines a flow channel nozzle.

Yet another aspect of the instant invention is directed to an accumulator for collecting a polarized gas. The accumulator comprises a primary flow channel having opposing inlet and exit ends, with the exit end being configured as a flow nozzle. The inlet end is detachably connected to a polarized gas collection path. The accumulator also includes an outer sleeve with a collection chamber aligned with and positioned adjacent to the flow nozzle. In a preferred embodiment, the accumulator includes a heat source such as the enclosed heating jacket as described above. In operation, the heat source is arranged in the device to heat the flow nozzle to prevent clogging or freezing of the polarized gas thereat. An accumulator with a nozzle in the primary flow path can help remove and trap all of the hyperpolarized gas from the inlet stream, reducing any waste of exiting polarized gases. The use of a nozzle improves localization of polarized gases such as $^{129}$Xe. Further, such a nozzle can minimize the heat load on accumulated $^{129}$Xe (thus lengthening its relaxation or decay time). The use of a warming jacket can allow the use of a nozzle in the cryogen flow area and can improve the operation or function of the nozzle by reducing any clogging in the nozzle area of the flow path.

An additional aspect of the present invention is directed to a method for collecting polarized noble gases. The method includes directing a gas mixture comprising a polarized noble gas into a collection path. The gas mixture is received into an accumulator positioned in the collection path. The accumulator has an inlet channel, a collection reservoir, and an exit channel. The collection reservoir is exposed to temperatures below the freezing point of the polarized noble gas. The polarized noble gas is trapped in a substantially frozen state in the collection reservoir. The remainder of the gas mixture is routed into the exit channel. A portion of the collection path is heated or warmed to facilitate the flow of the gas mixture therethrough. Preferably, the heating step includes the steps of introducing a gas separate from the gas mixture into a predetermined area of the inlet path, the predetermined area being contained apart from the inlet path. The gas is circulated separate from the gas mixture about a portion of the inlet path to provide conductive heat to at least a portion of the inlet path and thereby reduce the likelihood blockage along the inlet path attributed to the exposing step. Preferably, the heating is provided by circulating room temperature $N_2$ gas around the outside of at least a portion of the inlet path channel. The $N_2$ gas is then captured and vented to atmosphere away from the frozen accumulated noble gas.

Yet another aspect of the present invention is a method of thawing frozen polarized gas. In this method, a sealed container is provided. The container has an interior flow path and a collection chamber, the collection chamber is configured to hold frozen polarized gas therein. The frozen polarized gas is exposed to a magnetic field. A portion of the interior flow path adjacent the collection chamber is heated and the exterior of the sealed container is heated. Preferably, the thawing step is performed under pressure such that a substantial portion of the frozen noble gas is liquified during thawing of the frozen polarized gas. In a preferred embodiment, the container includes two valves, and after the frozen product is liquified, at least one of the valves is opened to decrease the pressure in the container causing the liquified gas to rapidly become gaseous. At this point, the flow of the gas is preferably directed to a patient. This step is typically accomplished by collecting the gas in a bag or other type of receptacle and delivering it to the patient. This method quickly thaws the frozen gas and minimizes the time the polarized gas spends in the transition phase which can improve the polarization levels retained upon thaw. Further, the instant thawing method can decrease the thawing time over conventional methods to less than 10 seconds for single patient MRI doses. In a preferred embodiment, the $^{129}$Xe gas mixture which is introduced into the polarizer includes a minimal amount of $^{131}$Xe to minimize decay associated with the $^{131}$Xe induced relaxation of the $^{129}$Xe isotope.

Yet another aspect of the present invention relates to a method of extending the useful polarized life of a polarized gas product. The method includes the steps of providing a magnetic field and freezing a polarized gas in the presence of the magnetic field. The polarized gas is sealed in a containment device or vessel. The frozen polarized gas is then thawed at a desired time. A substantial portion of the frozen gas is liquified under pressure in the sealed container. Preferably, the thawing step includes the heating steps as described above (heating both an interior and exterior of the sealed container). In any event, in one embodiment, the containment device is depressurized causing the liquid to become gas. More preferably, the depressurizing step is carried out by opening the containment device to a collection vessel and allowing the liquid to expand into a gas phase during delivery of the polarized gas to an end user.

Advantageously, such a method can increase the polarization level in the thawed polarized gas over conventional processing methods. Indeed, the instant invention can double the polarization levels retained in gas samples processed by conventional methods. Further and additionally advantageously, the instant invention provides an improved accumulator which can improve the accumulation and the preservation of the hyperpolarized state of the noble gas. Conventional thawing and accumulation techniques significantly reduced polarizations below predicted values (typically to about only 12.2% from its starting polarization levels at 900 sccm—losing 87.8% of its starting polarization). The instant invention can improve the preservation of the polarization substantially. For example, the improved accumulation and thawing methods can retain at least 30% or more (and preferably about 40%–50%) post-thaw polarization from the initial pre-frozen polarization levels ("the polarization retention fraction"). Further, the instant invention can provide polarization levels at 10% or more at the time of delivery to a patient or end user. In addition, the instant invention can collect additional amounts of polarized gas in a period by improving the delivery path and reducing the potential of the cold finger to block with frozen gas and the like during collection.

The foregoing and other objects and aspects of the present invention are explained in detail herein.

BRIEF DESCRIPTION OF THE DRAWINGS

FIG. 13 graphically illustrates exemplary polarization levels of polarized gas before freezing and after thawing according to the present invention.

FIG. 13A graphically illustrates predicted and experimental exemplary polarization levels of polarized xenon corresponding to the polarization flow rate for post-thaw experimental data taken when the xenon is processed according to the present invention.

DETAILED DESCRIPTION OF THE PREFERRED EMBODIMENTS

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. Layers and regions may be exaggerated for clarity. In the description of the present invention that follows, certain terms are employed to refer to the positional relationship of certain structures relative to other structures. As used herein the term "forward" and derivatives thereof refer to the general direction the gas mixture travels as it moves through the hyperpolarizer unit; this term is meant to be synonymous with the term "downstream" which is often used in manufacturing environments to indicate that certain material being acted upon is farther along in the manufacturing process than other material. Conversely, the terms "rearward" and "upstream" and derivatives thereof refer to the directions opposite, respectively, the forward and downstream directions. Also, as described herein, polarized gases are collected, frozen, thawed, and used in MRI spectroscopy or MRI applications. For ease of description, the term "frozen polarized gas" means that the polarized gas has been frozen into a solid state. The term "liquid polarized gas" means that the polarized gas has been or is being liquefied into a liquid state. Thus, although each term includes the word "gas", this word is used to name and descriptively track the gas which is produced via a hyperpolarizer to obtain a polarized "gas" product. Thus, as used herein, the term gas has been used in certain places to descriptively indicate a hyperpolarized noble gas product and may be used with modifiers such as solid, frozen, and liquid to describe the state or phase of that product.

Various techniques have been employed to accumulate and capture polarized gases. For example, U.S. Pat. No. 5,642,625 to Cates et al., describes a high volume hyperpolarizer for spin polarized noble gas and U.S. patent application Ser. No. 08/622,865 to Cates et al. describes a cryogenic accumulator for spin-polarized $^{129}$Xe. These references are hereby incorporated by reference as if recited in full herein. As used herein, the terms "hyperpolarize" "polarize", and the like, mean to artificially enhance the polarization of certain noble gas nuclei over the natural or equilibrium levels. Such an increase is desirable because it allows stronger imaging signals corresponding to better MRI images of the substance and a targeted area of the body. As is known by those of skill in the art, hyperpolarization can be induced by spin-exchange with an optically pumped alkali-metal vapor or alternatively by metastability exchange. See Albert et al., U.S. Pat. No. 5,545,396.

Figure 1:
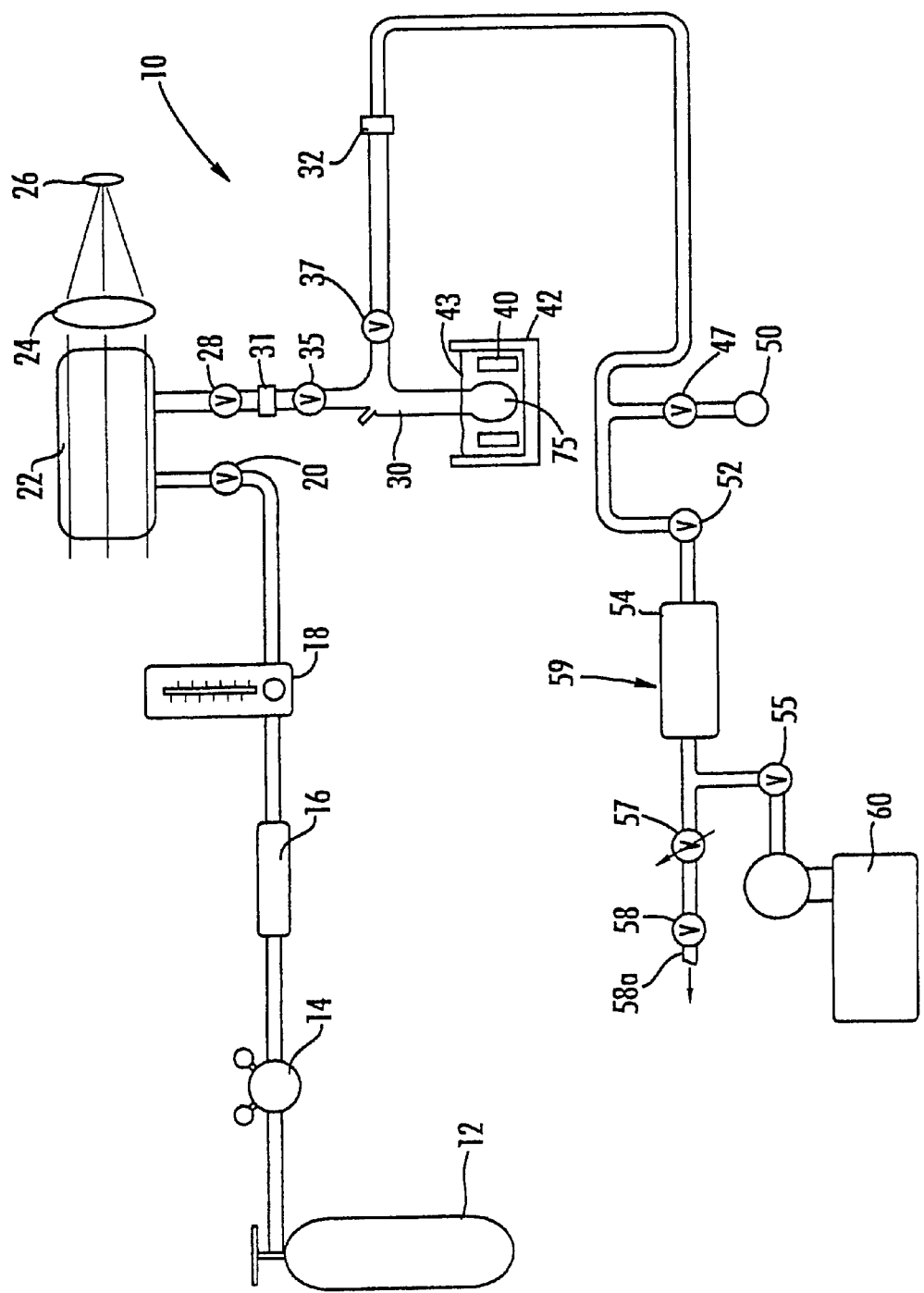
FIG. 1 is a schematic illustration of a hyperpolarizer apparatus according to one embodiment of the present invention.

Referring to the drawings, FIG. 1 illustrates a preferred hyperpolarizer unit 10. This unit is a high volume unit which is configured to continually produce and accumulate spin-polarized noble gases, i.e., the flow of gas through the unit is substantially continuous. As shown, the unit 10 includes a noble gas supply 12 and a supply regulator 14. A purifier 16 is positioned in the line to remove impurities such as water vapor from the system as will be discussed further below. The hyperpolarizer unit 10 also includes a flow meter 18 and an inlet valve 20 positioned upstream of the polarizer cell 22. An optic light source such as a laser 26 (preferably a diode laser array) is directed into the polarizer cell 22 through various focusing and light distributing means 24, such as lenses, mirrors, and the like. The light source is circularly polarized to optically pump the alkali metals in the cell 22. An additional valve 28 is positioned downstream of the polarizer cell 22.

Next in line, as shown in FIG. 1, is a cold finger or accumulator 30. The accumulator 30 is connected to the hyperpolarizer unit 10 by a pair of releasable mechanisms such as threaded members or quick disconnects 31, 32. This allows the accumulator to be easily detached, removed, or added, to and from the system 10. The accumulator 30 is operably associated with a cold source or refrigeration means 42. Preferably, and as shown, the cold source 42 is a liquid cryogen bath 43. The accumulator will be discussed in more detail hereinbelow.

A vacuum pump 60 is in communication with the system. Additional valves to control flow and direct exit gas are shown at various points (shown as 52, 55). A shut-off valve 47 is positioned adjacent an "on-board" exit gas tap 50. Certain of the valves downstream of the accumulator 30 are used for "on-board" thawing and delivery of the collected polarized gas as will be described further below. The system also includes a digital pressure transducer 54 and a flow control means 57 along with a shut-off valve 58. The shut-off valve 58 preferably controls the flow of gas through the entire system or unit 10; it is used to turn the gas flow on and off, as will be described below. As will be understood by those of skill in the art, other flow control mechanisms, devices (analog and electronic) may be used within the scope of the present invention.

In operation, a gas mixture is introduced into the system at the gas source 12. As shown in FIG. 1, the source 12 is a pressurized gas tank which holds a pre-mixed gas mixture. The gas mixture includes a lean noble and buffer gas mixture gas (the gas to be hyperpolarized is present as a relatively small amount in the pre-mixed gas mixture). Preferably, for producing hyperpolarized $^{129}$Xe, the pre-mixed gas mixture is about 95–98% He, about 5% or less $^{129}$Xe, and about 1% N$_2$.

It is also preferred that the pre-mixed gas mixture comprises a minimal amount of the xenon –131 (or $^{131}$Xenon) isotope (reduced from its natural levels). In nature, the typical xenon isotopic abundances are as follows:

TABLE I

| Isotope | Abundance | Nuclear Spin |
|---------|-----------|--------------|
| $^{124}$Xe | 0.1% | 0 |
| $^{126}$Xe | 0.09% | 0 |
| $^{128}$Xe | 1.91% | 0 |
| $^{129}$Xe | 26.4% | ½ |
| $^{130}$Xe | 4.1% | 0 |
| $^{131}$Xe | 21.2% | 3/2 |
| $^{132}$Xe | 26.9% | 0 |
| $^{134}$Xe | 10.4% | 0 |
| $^{136}$Xe | 8.9% | 0 |

"Enriched" $^{129}$Xe mixtures are used to provide sufficient amounts of the $^{129}$Xe gas for the hyperpolarized gas mixture. As used herein, the form "enriched" means increasing the abundance of $^{129}$Xe over its natural abundance level. However, the enriched $^{129}$Xe typically also includes other Xenon isotopes. Unfortunately, at least one particular isotope—$^{131}$Xe can interact with frozen $^{129}$Xe (particularly at low temperatures such as 4.2° K) in a manner which can cause the $^{129}$Xe to depolarize. At low temperatures, the $^{131}$Xe acts like a "spin-sink" to absorb or decay the $^{129}$Xe polarization and becoming a potentially dominant relaxation mechanism at the crystal grain boundaries of the frozen "solid" $^{129}$Xe polarized gas.

As shown in Table I above, $^{131}$Xe is an isotope with a nuclear spin greater than one-half. As such, it has a "quadruple moment" which means that $^{131}$Xe is able to relax by interacting with electric field gradients. See Gatzke et al., *Extraordinarily slow nuclear spin relation in frozen laser-polarized 129Xe,* Phys. Rev. Lett. 70, pp. 690–693 (1993).

It has been suggested that at 4.2° K, the dominant solid phase relaxation mechanism is "cross-relaxation" between the $^{129}$Xe and $^{131}$Xe isotopes at the crystal grain boundaries. In addition, where the "frozen" or "solid" $^{129}$Xe gas takes on a form similar to a flake (such as a snowflake) the form has a relatively large surface area. Unfortunately, this relatively large surface area can also allow greater depolarizing interactions with the $^{131}$Xe. It is believed that the greatest or "most-efficient" interchange is at the crystal grain boundaries because that is typically where the electric fields are strongest. This electric field strength can then allow the $^{131}$Xe nuclear spin flip energy to become nearly the same as the $^{129}$Xe nuclear spin flip energy.

Examples of enriched $^{129}$Xe mixtures with a reduced $^{131}$Xe isotope content are given below.

EXAMPLE 1

82.3% Enriched $^{129}$Xe Gas Mixture.

| Isotope | Abundance | Nuclear Spin |
|---------|-----------|--------------|
| $^{124}$Xe | 0.47% | 0 |
| $^{126}$Xe | 0.43% | 0 |
| $^{128}$Xe | 8.41% | 0 |
| $^{129}$Xe | 82.3% | ½ |
| $^{130}$Xe | 4.52% | 0 |
| $^{131}$Xe | 3.45% | 3/2 |
| $^{132}$Xe | 0.36% | 0 |
| $^{134}$Xe | 0.01% | 0 |
| $^{136}$Xe | 0.01% | 0 |

EXAMPLE 2

47.2% Enriched $^{129}$Xe Gas Mixture.

| Isotope | Abundance | Nuclear Spin |
|---|---|---|
| $^{124}$Xe | 0.14% | 0 |
| $^{126}$Xe | 0.28% | 0 |
| $^{128}$Xe | 52.0% | 0 |
| $^{129}$Xe | 47.2% | ½ |
| $^{130}$Xe | 0.22% | 0 |
| $^{131}$Xe | 0.09% | 3/2 |
| $^{132}$Xe | 0.03% | 0 |
| $^{134}$Xe | 0.02% | 0 |
| $^{136}$Xe | 0.02% | 0 |

In a preferred embodiment, when the collected polarized $^{129}$Xe will be exposed to cold temperatures and frozen, the enriched $^{129}$Xe gas mixture preferably includes less than about 3.5% $^{131}$Xe, and more preferably less than about 0.1% $^{131}$Xe.

In any event, the gas "enriched" mixture is passed through the purifier 16 and introduced into the polarizer cell 22. The valves 20, 28 are on/off valves operably associated with the polarizer cell 22. The gas regulator 14 preferably steps down the pressure from the gas tank source 12 (typically operating at 13,780.2 kPa (2000 psi or 136 atm)) to about 608–1013.25 kPa (6–10 atm) for the system. Thus, during accumulation, the entire manifold (conduit, polarized cell, accumulator, etc.) is pressurized to the cell pressure (about 608–1013.25 kPa (6–10 atm)). The flow in the unit 10 is activated by opening valve 58 and is controlled by adjusting the flow control means 57.

The typical residence time of the gas in the cell 22 is about 10–30 seconds; i.e., it takes on the order of 10–30 seconds for the gas mixture to be hyperpolarized while moving through the cell 22. The gas mixture is preferably introduced into the cell 22 at a pressure of about 608–1013.25 kPa (6–10 atm). Of course, with hardware capable of operating at increased pressures, operating pressures of above 1013.25 kPa (10 atm), such as about 2026.5–3039.75 kPa (20–30 atm) are preferred to pressure broaden the Rb and absorb up to 100% of the optical light. In contrast, for laser linewidths less than conventional linewidths, lower pressures can be employed. The polarizer cell 22 is a high pressure optical pumping cell housed in a heated chamber with apertures configured to allow entry of the laser emitted light. Preferably, the hyperpolarizer unit 10 hyperpolarizes a selected noble gas such as $^{129}$Xe (or $^{3}$He) via a conventional spin-exchange process. A vaporized alkali metal such as rubidium ("Rb") is introduced into the polarizer cell 22. The Rb vapor is optically pumped via an optic light source 26, preferably a diode laser.

The unit 10 employs helium buffer gas to pressure broaden the Rb vapor absorption bandwidth. The selection of a buffer gas is important because the buffer gas—while broadening the absorption bandwidth—can also undesirably impact the alkali metal-noble gas spin-exchange by potentially introducing an angular momentum loss of the alkali metal to the buffer gas rather than to the noble gas as desired. In a preferred embodiment, $^{129}$Xe is hyperpolarized through spin exchange with the optically pumped Rb vapor. It is also preferred that the unit 10 uses a helium buffer gas with a pressure many times greater than the $^{129}$Xe pressure for pressure broadening in a manner which minimizes Rb spin destruction.

As will be appreciated by those of skill in the art, Rb is reactive with $H_2O$. Therefore any water or water vapor introduced into the polarizer cell 22 can cause the Rb to lose laser absorption and decrease the amount or efficiency of the spin-exchange in the polarizer cell 22. Thus, as an additional precaution, an extra filter or purifier (not shown) can be positioned before the inlet of the polarizer cell 22 with extra surface area to remove even additional amounts of this undesirable impurity in order to further increase the efficiency of the polarizer.

Figure 2:
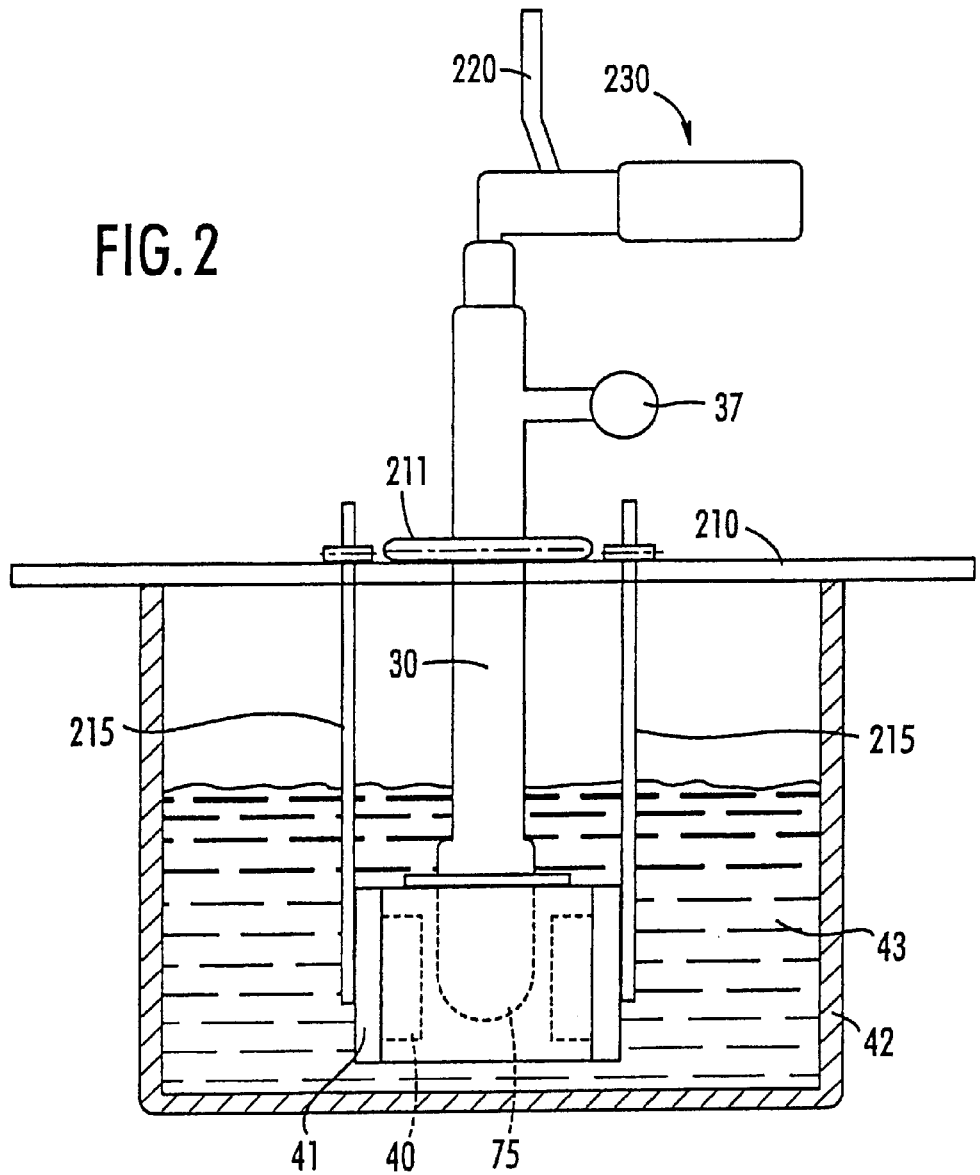
FIG. 2 is a side perspective view of an accumulator or "cold finger" of the apparatus of FIG. 1 partially immersed in a liquid cryogen according to one embodiment of the present invention.

Hyperpolarized gas, together with the buffer gas mixture, exits the polarizer cell 22 and enters the accumulator 30. Referring now to FIGS. 3–7, the polarized gas and buffer gas are directed down a primary flow path 80 and into a collection reservoir 75 located at the bottom of the accumulator 30. In operation, at the lower portion of the accumulator 30a, the hyperpolarized gas is exposed to temperatures below its freezing point and collected as a frozen product 100 in the reservoir 75. The remainder of the gas mixture remains gaseous and exits the primary flow path 80 and the reservoir 75 by counterflowing in an exit path 90 different from the primary flow path 75 such that it is directed out of the accumulator 30. The accumulator 30 will be discussed in more detail below. The hyperpolarized gas is collected (as well as stored, transported, and preferably thawed) in the presence of a magnetic field, generally on the order of at least 500 Gauss, and typically about 2 kiloGauss, although higher fields can be used. Lower fields can potentially undesirably increase the relaxation rate or decrease the relaxation time of the polarized gas. As shown in FIG. 2, the magnetic field is provided by permanent magnets 40 positioned about a magnetic yoke 41.

The hyperpolarizer unit 10 can also use the temperature change in the outlet line between the heated pumping cell 22 and the refrigerated cold trap or accumulator 30 to precipitate the alkali metal from the polarized gas stream in the conduit above the accumulator 30. As will be appreciated by one of skill in the art, the alkali metal can precipitate out of the gas stream at temperatures of about 40° C. The unit can also include an alkali metal reflux condenser (not shown). Preferably, the refluxing condenser employs a vertical refluxing outlet pipe, which is kept at room temperature. The gas flow velocity through the refluxing pipe and the size of the refluxing outlet pipe is such that the alkali metal vapor condenses and drips back into the pumping cell by gravitational force. In any event, it is desirable to remove the alkali metal such that the product is non-toxic and comply with regulatory standards (for example at least to a level at or below 10 ppb) prior to delivering polarized gas to a patient.

Optionally, an intermediate cold trap can also be positioned between the exit of the polarizer cell 22 and the cold finger 30. The temperature of the intermediate cold trap (not shown) will preferably be designed to trap out any alkali metal (e.g. Rb) while leaving the noble gas and carrier gas (es) free to reach the cold finger 30. This can be important for in vivo applications where it is important to remove the Rb from the hyperpolarized gas (i.e., remove the Rb to a level such that no more than trace amounts such as on the order of one ppb or less remains in the hyperpolarized gas when delivered to a patient).

Once a desired amount of hyperpolarized gas has been collected in the accumulator 30, the accumulator can be detached or isolated from the system. In a preferred embodiment, valve 28 is closed, leaving the cell 22 pressurized. This allows the accumulator 30 and the downstream plumbing to begin to depressurize because the flow valve 58 is open. Preferably, the unit 10 downstream of the valve 28 is allowed to depressurize to about 1.5 atm before the flow valve 58 is closed. After closing the flow valve 58, valve 55 can be opened to evacuate the remaining gas in the manifold. Once the outlet plumbing is evacuated, valves 35 and 37 are closed. If the collected gas is to be distributed "on board", i.e., without removing the accumulator 30 from the unit 10, a receptacle such as a bag or other vessel can be attached to the outlet 50. The valve 47 can be opened to evacuate the attached bag (not shown). Once the bag is evacuated and the gas is ready to thaw, valve 52 can be optionally closed. This minimizes the contact of the polarized gas with the pressure transducer region 59 of the unit 10. This region typically includes materials that have a depolarizing effect on the polarized gas. Thus, long contact times with this region may promote relaxation of the polarized gas.

If the valve 52 is not closed, then valve 55 is preferably closed to prevent the evacuation of polarized thawed gases. It is also preferred that the flow channels on the downstream side of the cell 22 are formed from materials which minimize the decaying effect on the polarized state of the gas. Coatings can also be used such as those described in U.S. Pat. No. 5,612,103, the disclosure of which is hereby incorporated by reference as if recited in full herein. In the "on-board" thaw operation, valve 37 is opened to let the gas out. It then proceeds through valve 47 and exits outlet 50.

In the "detached" or "transported accumulator" thaw mode, accumulator first and second isolation valves 35, 37 are closed after the depressurization and evacuation of the accumulator 30. Evacuating the accumulator 30 allows any residual gas in the accumulator to be removed. Leaving residual gas in the accumulator 30 with the frozen polarized gas may contribute to the heat load on the frozen gas, possibly raising the temperature of the frozen gas and potentially shortening the relaxation time. Thus, in a preferred embodiment, after depressurization and evacuation and closing the isolation valves 35, 37, the accumulator 30 is disconnected from the unit 10 via release points 31, 32.

It is also preferred that the accumulator include O-rings in grooves (FIG. 2, 220) to assist in sealing the quick connects (or other attaching means) to the conduit lines in the system. This type of O-ring/groove sealing mechanism can help assure the seals integrity even at the elevated operating pressures (i.e., 608–1013.25 kPa (6–10 atm)) and greater) of the unit Similarly, if CHEM-THREADS™ (manufactured by ChemGlass, Inc. Vineland, N.J.) or similar attachment means are used, it is preferred that they be configured to hold pressures consistent with the operating pressures of the system. Examples of suitable isolation valves 35, 37 include KIMBLE KONTES Valves 826450-004, 826460-0004 located in Vineland, N.J.

The isolation valves 35, 37 are in communication with the primary flow channel 80 and the buffer gas exit channel 90 respectively and each can adjust the amount of flow therethrough as well as close the respective paths to isolate the accumulator from the system 10 and the environment. After the filled accumulator 30 is removed, another accumulator can be easily and relatively quickly attached to the release points 31, 32. Preferably, when attaching the new accumulator 30, the outlet manifold is evacuated using valve 55 (with valves 52, 35, 37 open). When a suitable vacuum is achieved (such as about 13.3 Pa (100 milliTorr)) which typically occurs within about one minute or so, valve 55 is closed. Valve 28 is then re-opened which repressurizes the outlet manifold to the operating cell pressure. Valve 58 is then opened to resume flow in the unit 10. Preferably, once flow resumes, liquid nitrogen is applied to the accumulator 30 to continue collection of the hyperpolarized gas. Typically such a changeover takes on the order of less than about five minutes. Thus, a preferred hyperpolarizer unit 10 is configured to provide a continuous flow of hyperpolarized $^{129}$Xe gas for continuous production and accumulation of same.

Turning now to FIG. 2, an accumulator and magnet yoke assembly 230 is shown. The accumulator 30 is supported by a support platform 210 positioned over the cryogen bath 43. A pair of plates 215 longitudinally extend from the support platform 210 and connect to the magnet yoke 41. The magnet yoke 41 is positioned adjacent to and in close proximity to the collection reservoir 75 of the accumulator 30 to provide the desired magnetic field to the collected polarized gas. As shown, the accumulator 30 includes a support contact portion 211, which is configured to rest against the support platform 210.

The Accumulator

Figure 3:
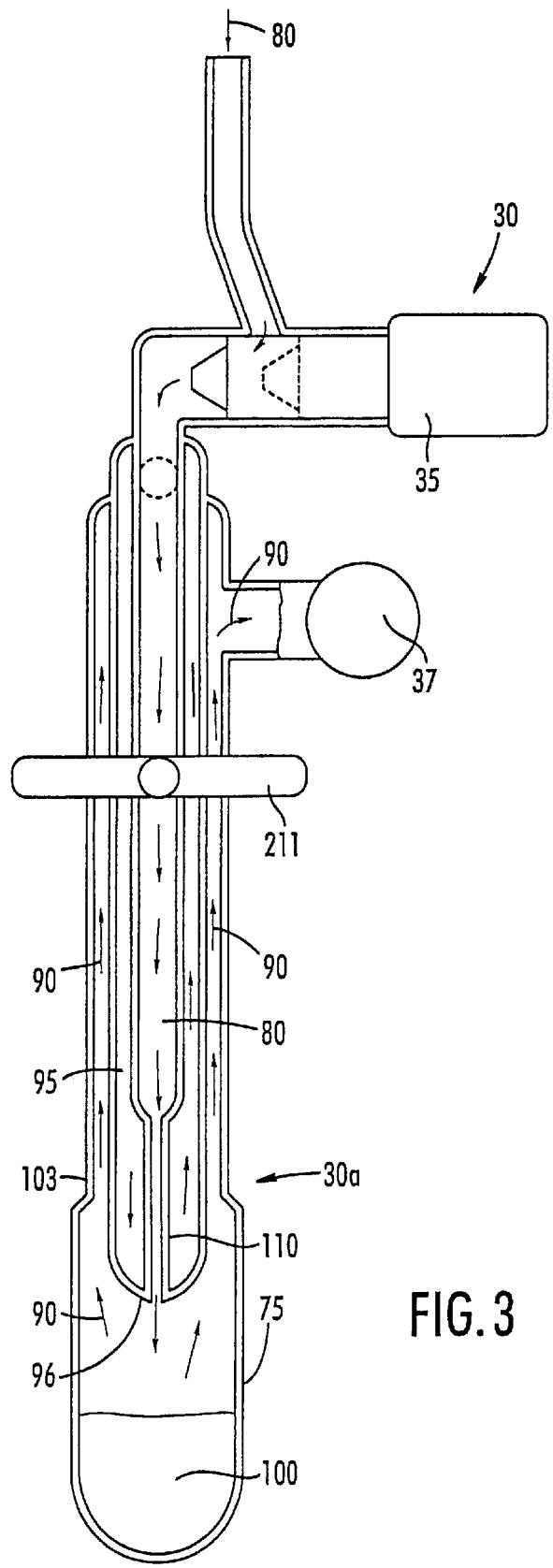
FIG. 3 is a cross-sectional side view of an accumulator of FIG. 2 according to one embodiment of the present invention.
Figure 4:
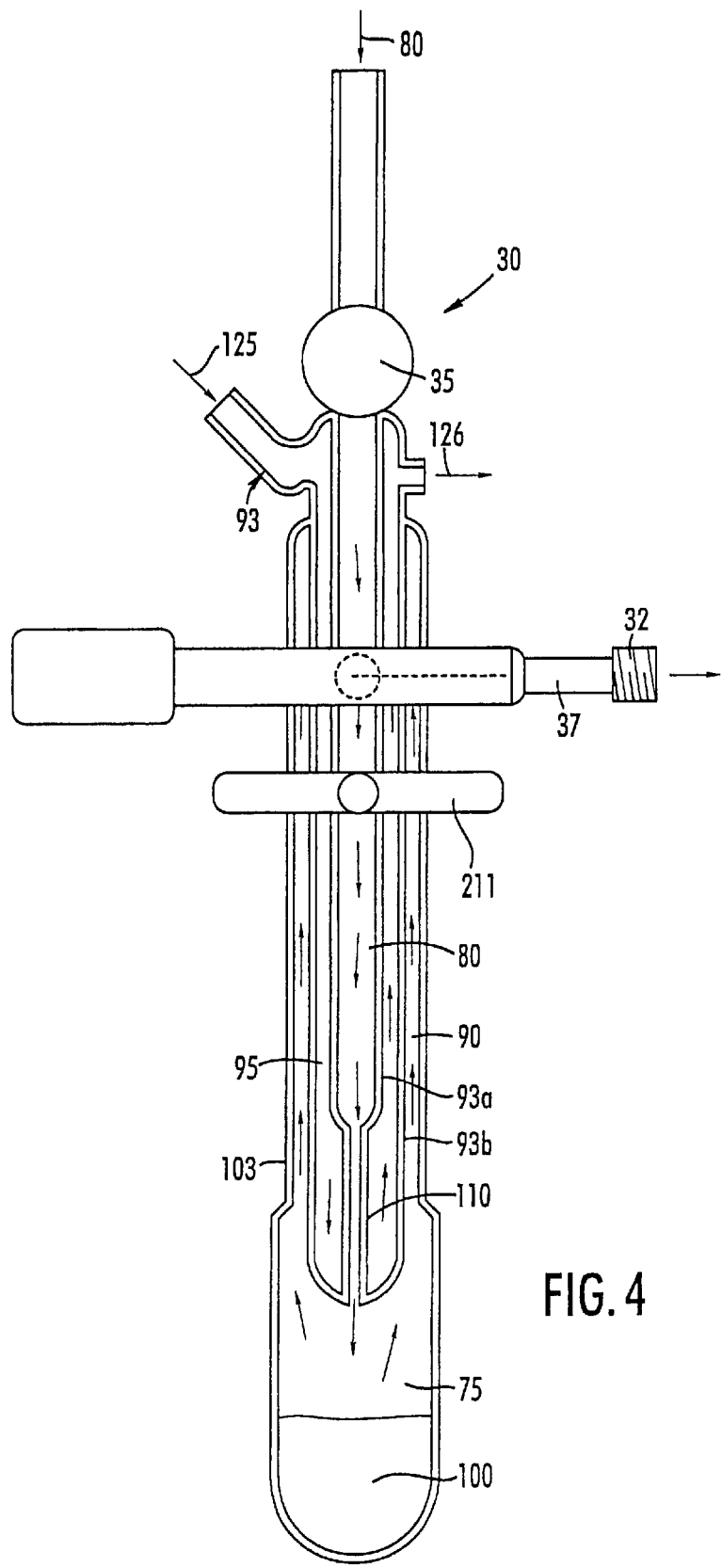
FIG. 4 is a front view of the accumulator illustrated in FIG. 3.

FIGS. 3 and 4 show one embodiment of an accumulator 30 according to the instant invention. As shown, the accumulator 30 includes a central primary flow path 80, a secondary flow path 95, and an exit buffer gas channel 90. The secondary flow path or channel 95 is positioned intermediate of the primary flow path channel 80 and the buffer exit channel 90. In a preferred embodiment, the accumulator 30 includes a nozzle 110 at the lower end of the primary flow path. The nozzle 110 can help improve localization of the hyperpolarized gas as it impacts the cold surfaces of the reservoir 75. The nozzle 110 may also allow Joule-Thompson expansion of the cooling of the gas stream to well below the freezing point of the hyperpolarized gas, advantageously minimizing the heat load on the stationary and collected hyperpolarized gas and thereby, potentially lengthening its relaxation time. In any event, the accumulator 30 is preferably immersed in the cryogen bath 43 such that the reservoir 75 and about 7.62–15.24 cm (3–6 inches) of the tube is immersed. If submerged in liquid nitrogen, the exterior wall of the outer sleeve 103 and the exterior wall or the reservoir 75 will be at about 77° K. The freezing point of Xenon is approximately 160° K. Thus, upon exiting the primary flow path 80, the hyperpolarized gas hits the cold surface and freezes into the reservoir 75 while the buffer gases exit the accumulator via the exit channel 90. The reservoir can include a surface coating to help prevent relaxation caused by the polarized gas's contact with same. See U.S. Pat. No. 5,612,103, "Improved Coatings for the Production of Hyperpolarized Noble Gases". Alternatively, the container can be formed from or include other materials such as high purity non-magnetic metallic films. See co-pending and co-assigned patent application Ser. No. 09/126,448, entitled Containers for Hyperpolarized Gases and Associated Methods, which is hereby incorporated by reference as if recited in full herein.

As shown in FIG. 4, the secondary flow path 95 has an inlet and outlet 125, 126, respectively, positioned about 180° apart at a top portion of the accumulator 30. Of course, as will be appreciated by one of skill in the art, alternative arrangements of the secondary flow path inlet and outlet 125, 126 can also be employed. Preferably, the inlet and outlet 125, 126 are configured to be above the cryogen bath 43 or other refrigeration means when the accumulator 30 is assembled thereto. Except for its respective inlet and vent ports 125, 126, the secondary flow path 95 is enclosed and separate from the primary flow path 80 and the exit gas path 90. As such, the secondary flow path 95 includes a sealed closed end 96.

Figure 6:
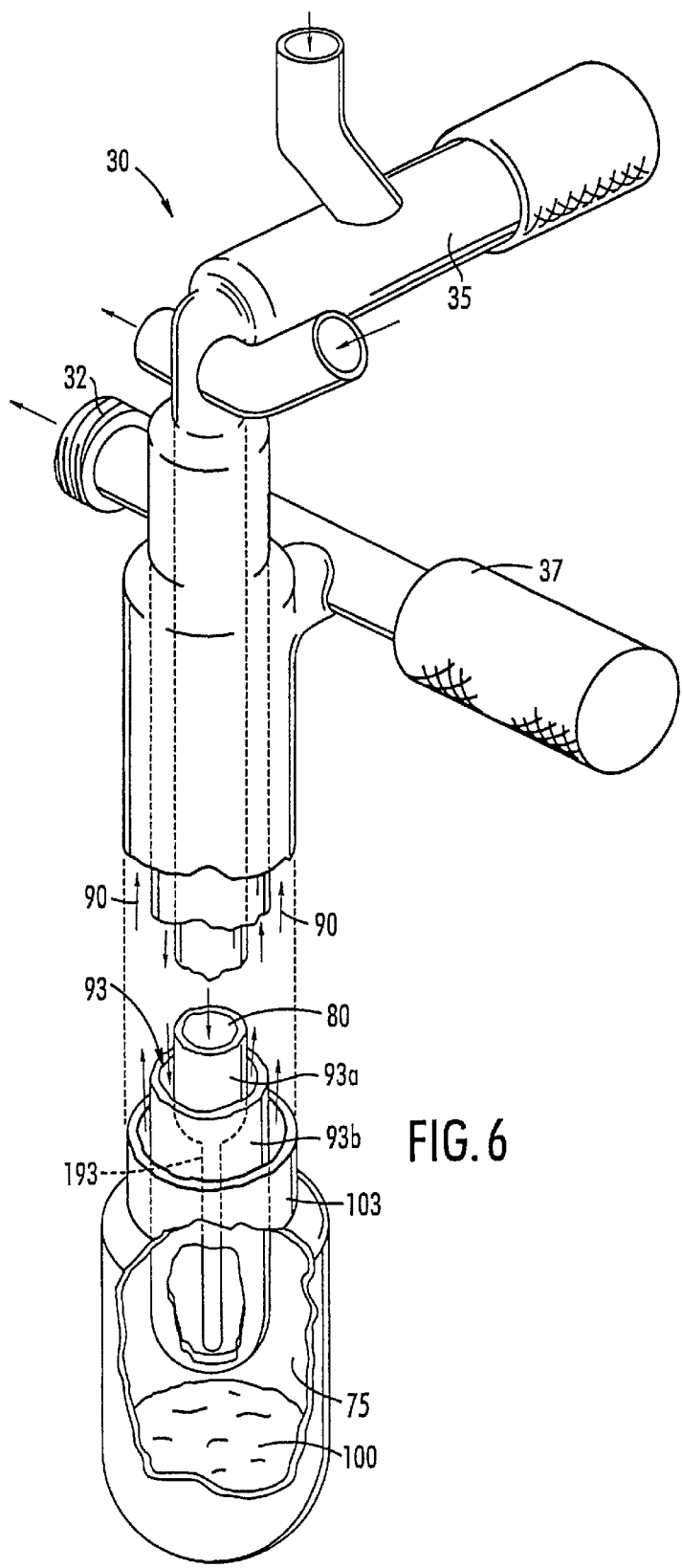
FIG. 6 is a partial cutaway perspective view of the accumulator illustrated in FIG. 3.

In operation, as shown in FIG. 6, the secondary flow path 95 provides heat to a region of the accumulator 30.

Preferably, the secondary flow path defines a heating jacket 93. The heating jacket 93 is configured to provide a contained warm stream of a fluid, preferably a gas, around the primary flow path 80. More preferably, the heating jacket 93 directs warm or ambient temperature nitrogen down the secondary flow path to an area adjacent the lower portion of the primary path 80; that is, the portion of the secondary path is in close proximity to or adjacent the reservoir 75. In a preferred embodiment, the warming gas in the heating jacket 93 is directed to the nozzle 110 area of the primary flow path 80 via the secondary flow path 95. Advantageously, such a warming gas can compensate for the undesirable tendency of this area of the primary flow path to freeze and clog due to frozen gases trapped in the flow path 80. Further and advantageously, this configuration can also minimize any associated heat load which is directed into the reservoir 75 and on the collected frozen polarized gas. The clogging problem can be particularly troublesome in accumulators with nozzle designs, as even small amounts of build up in the reduced exit area of the nozzle 110 can block the primary flow path 80 and decrease and even prevent further collection of polarized gas. "Warming" as used herein can be the application of heat at any temperature above the freezing point of selected polarized gas, i.e. above 160° K for $^{129}$Xe.

Generally stated, the relaxation time of solid polarized gas (especially $^{129}$Xe) is strongly dependent on the temperature of the frozen gas. Stated differently, the lower the temperature of the frozen gas, the longer the relaxation time. Thus, it is important to minimize the heat load on the accumulated frozen gas. The heat load presented by the gas stream directed down the primary flow path 80 is largely attributed to the need to cool the buffer gas from room temperature to the cryogenic temperature (as described herein liquid nitrogen (LN$_2$) or 77° K. This heat load is estimated to be on the order of 2 W. Thus, in order to minimize the heat load on the accumulated polarized $^{129}$Xe, it is desirable to cool the gas steam to close to (but above) the freezing temperature of the polarized gas prior to the exit point of the nozzle 110. For $^{129}$Xe, the buffer gas is preferably cooled to just above 160° K, below which the Xe can freeze in the nozzle potentially causing a clog or blockage. Advantageously, cooling the exit gas to 160° K can cut the heat load on the frozen polarized gas by as much as 50%. The configuration of the instant invention allows this exit channel to be so cooled through the counter-flow of the buffer gas. Advantageously, this cooling counter-flow does not overly expose the nozzle 110 to low temperatures because the nozzle 110 or most susceptible area of the flow path 80 is separated from the exit channel by the heating jacket or secondary flow channel 95.

Referring again to FIG. 4, as shown, the primary flow path 80 is defined by the shape of the inner wall 93a of the heating jacket 93. Preferably, the inner wall 93a circumferentially extends around an opening to define the primary flow path 80. Similarly, the outer wall 93b of the heating jacket 93 together with the outer sleeve 103 of the accumulator 30 defines the buffer exit path 90. As shown in FIG. 6, in a preferred embodiment, the inner wall 93a, the outer wall 93b and the outer sleeve 103 are radially aligned. The inner wall of the heating jacket 93 includes a stepped down portion 193 with a diameter less than the diameter of the preceding section of the inner wall. This stepped down portion is configured to provide the nozzle 110 in the primary flow path 80.

Figure 5:
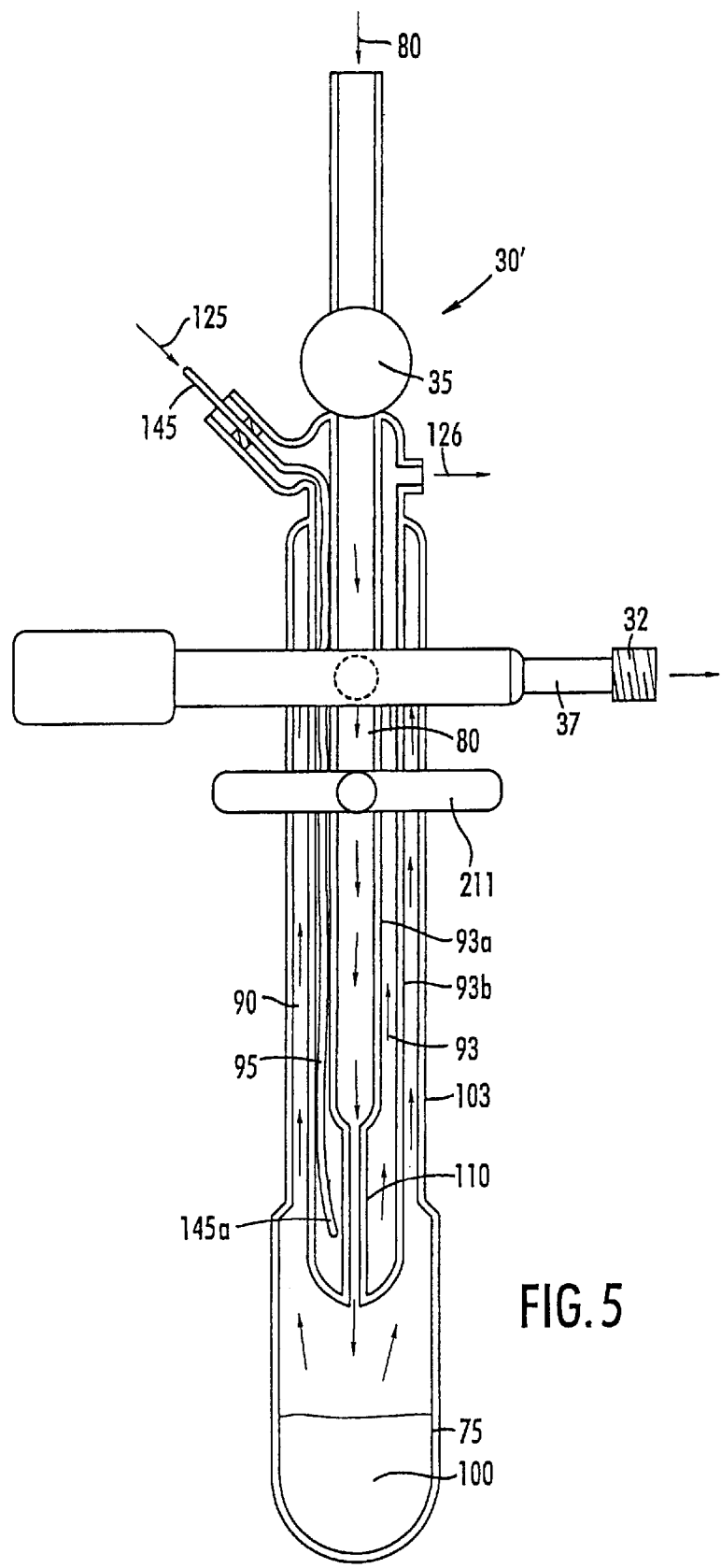
FIG. 5 is a cross-sectional side view of an additional embodiment of an accumulator of the present invention.
Figure 7:
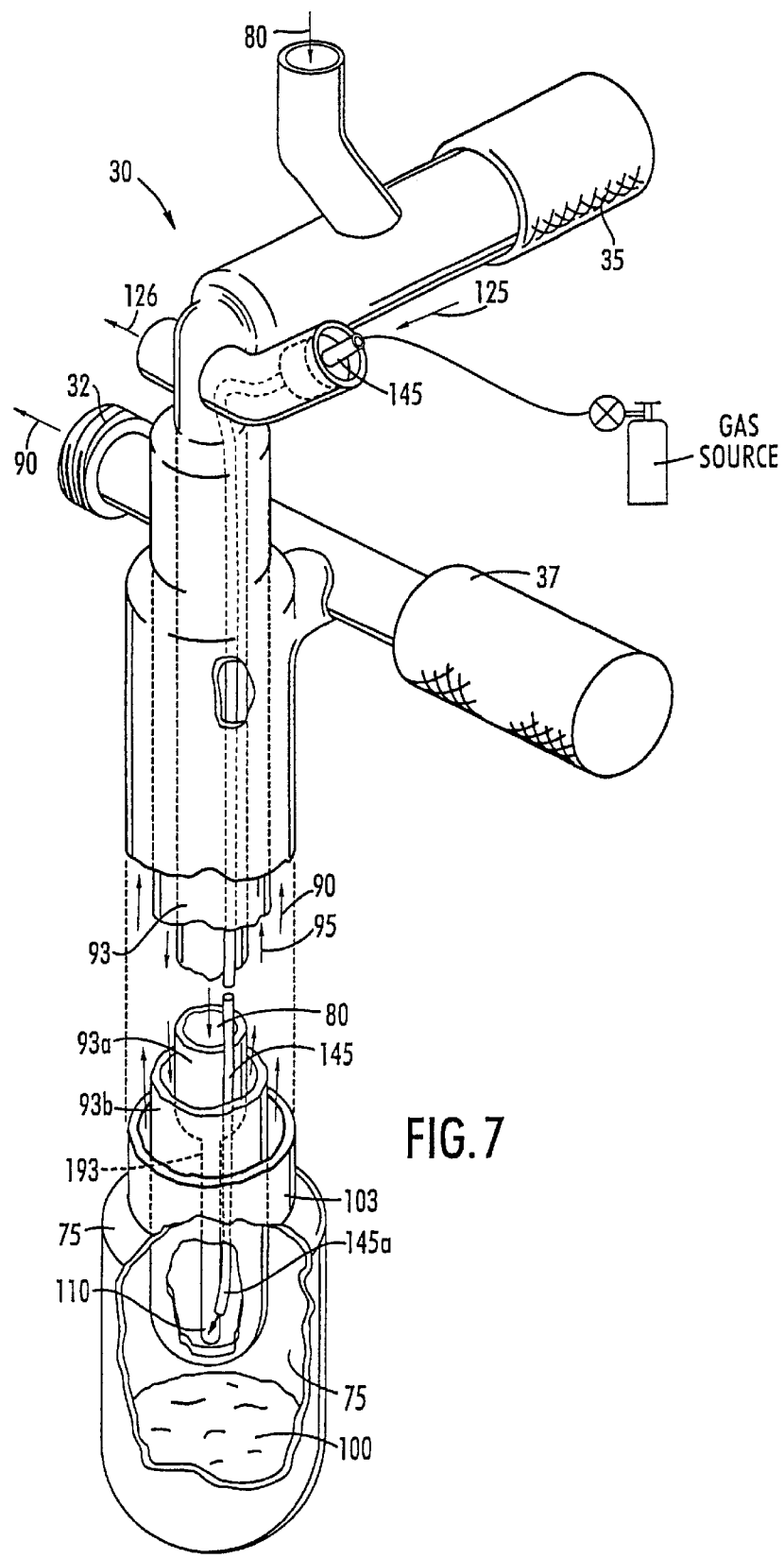
FIG. 7 is a partial cutaway perspective view of the accumulator illustrated in FIG. 5.

FIGS. 5 and 7 illustrate a preferred embodiment of an accumulator 30' according to the instant invention. As shown in this embodiment, the heating jacket 93 includes at least one elongated conduit 145 which extends along a major portion of the secondary flow path 95. As the conduit 145 is exposed to cryogenic temperatures, it should be made from suitable substantially non-depolarizing and cryo-accepting materials such as PTFE and the like. Suitable materials include materials which have a low temperature resistance. One example of a brand of such a material is TEFLON™ or metallic-film coated surfaces. The conduit 145 directs the warming gas down to the lower portion of the primary flow path 80, and more preferably directs the warming gas to the nozzle area 110 of the primary flow channel above the reservoir 75. As such, the lower end 145a of the conduit is preferably positioned adjacent the nozzle 110. Once released, the warming gas travels up the circumferentially extending secondary flow path 95 and exits at the outlet vent 126. This warming gas can counteract the cold/clogging effect the counter-flow of the cold buffer gas has on the primary flow path in the region susceptible to clogging as discussed above. Of course, additional heating jacket inlets, conduits, and vents (not shown) can also be employed within the scope of the invention.

Examples of suitable diameters of the primary flow path 80, the secondary flow path 95, and the buffer gas exit channel 90 are 6.35, 12.7, and 19.05 mm (0.25, 0.50, and 0.75 inches), respectively. In one embodiment the nozzle 110 extends along the primary flow path for about 25.4 mm (1.0 inches). Preferably, the accumulator 30 is formed from glass such as PYREX™ and is configured to withstand from about 608–1013.25 kPa (6–10 atm) or more of pressure.

In operation, it is preferred that, during accumulation of frozen hyperpolarized gas, the warming gas is introduced into the secondary channel at a rate of about 7.8658–47.2 ml/s (1–6 ft$^3$/hour), more preferably at the rate of about 15.732–39.329 ml/s (2–5 ft$^3$/hr), and still more preferably at a rate of about 23.597 ml/s (3 ft$^3$/hr). Preferably, during collection, the accumulator 30 operates at the same pressure as the optical pumping cell.

As discussed above, the preferred warming gas is a dry ambient temperature N$_2$ (N$_2$ has approximately two times the heat capacity of helium), but the invention is not limited thereto. Exemplary preferred temperatures of the warming gas are from about 10–26.7° C. (50°–80° F.), and more preferably from about 20–25.6° C. (68°–78° F.). In a preferred embodiment, a corresponding "heating gas" flow rate is set to a minimum level corresponding to a predetermined temperature of the warming gas; i.e., the minimum rate is set for a certain temperature below which a clog occurs, this minimum rate can be termed the "critical flow rate". If higher temperatures are used, lower flow rates will typically be required. Examples of other warming gases include, but are not limited to, helium, dry air, and the like. Preferably, if higher temperature "warming" gases are used a lower corresponding flow rate is used. In contrast, if lower temperature "warming" gases are used then a higher corresponding flow rate is used.

Advantageously, the instant invention can collect about 80–100% of the polarized gas in the gas stream. In addition, the instant invention can yield a polarized gas product with an extended useful life. This is attributed to the improved collection and/or thawing techniques which can yield a polarized gas product which retains greater polarization levels compared to conventional techniques as will be discussed further below.

Thawing

As noted above, a preferred embodiment of the instant invention employs a compact permanent magnet arrangement positioned around the hyperpolarized gas. Unfortunately, the magnetic field provided by such an arrangement can be somewhat inhomogeneous. As gas is thawed, this inhomogeneity can depolarize the hyperpolarized gas relatively quickly. Freshly thawed $^{129}$Xe is particularly susceptible to inhomogeneity induced decay ("loss of polarization"). For example, relaxation of gaseous $^{129}$Xe is particularly troublesome as it diffuses through inhomogeneous fields. This relaxation generally scales linearly with inverse pressure of the gas. That is, at low gas pressures, which occur at the beginning of the thawing process, the inhomogeneity (field gradients) induced relaxation effect is the strongest. (Relaxation of $^{129}$Xe at 101.325 kPa (1 atm) of gas pressure has been measured at just 22 seconds). The instant invention solves this problem by closing the isolating valves 35, 37 in the accumulator 30 during the initial thaw. As the polarized gas thaws, pressure builds up rapidly, quickly exceeding 1 atm and building further. As the pressure rises, the remaining solid $^{129}$Xe goes into liquid form rather than gaseous form. The liquid $^{129}$Xe is relatively insensitive to magnetic field gradients, inhomogeneity relaxation, temperature effects, and magnetic field strengths, thus making it one of the more robust forms of hyperpolarized $^{129}$Xe. Liquid $^{129}$Xe has typical relaxation times of about 20–30 minutes. See K. L. Sauer et al., *Laser Polarized Liquid Xenon*, Appl. Phys. Lett. (Accepted 1997). The liquid state further helps to quickly distribute heat to the remaining solid $^{129}$Xe, thus further speeding the thaw.

In a preferred embodiment, the heating jacket 93 can also improve the thawing process of the frozen polarized gas. The instant invention recognizes that it is important to rapidly transform the frozen polarized gas into a liquid state as both the solid and the gas states of Xenon are extremely sensitive to depolarization during the transition. For example, as solid or frozen $^{129}$Xe is warmed to near its melting point, the relaxation time is dramatically reduced from 3 hours at 77° K. to just a few seconds near the phase transition point. In addition, gaseous relaxation at temperatures just above the sublimation temperature of $^{129}$Xe is rapid, with an exponential dependence on temperature. For example, the relaxation time of gaseous $^{129}$Xe on a given surface at 160° K is only 3% as long as that at 300° K on the same surface. Further, during the early stages of thawing when the Xe gas pressure is low, the gaseous $^{129}$Xe is more susceptible to the inhomogeneity problems discussed above.

Conventionally, heat has been supplied to the exterior of the accumulator during thawing. As the frozen hyperpolarized gas began to thaw it would freeze again, such as on the exit point of the primary flow path 80. This could cause the $^{129}$Xe to freeze and thaw more than once during the thawing process, as well as causing the polarized gas product to spend more time around the sensitive transition phase where relaxation is more rapid.

Figure 8:
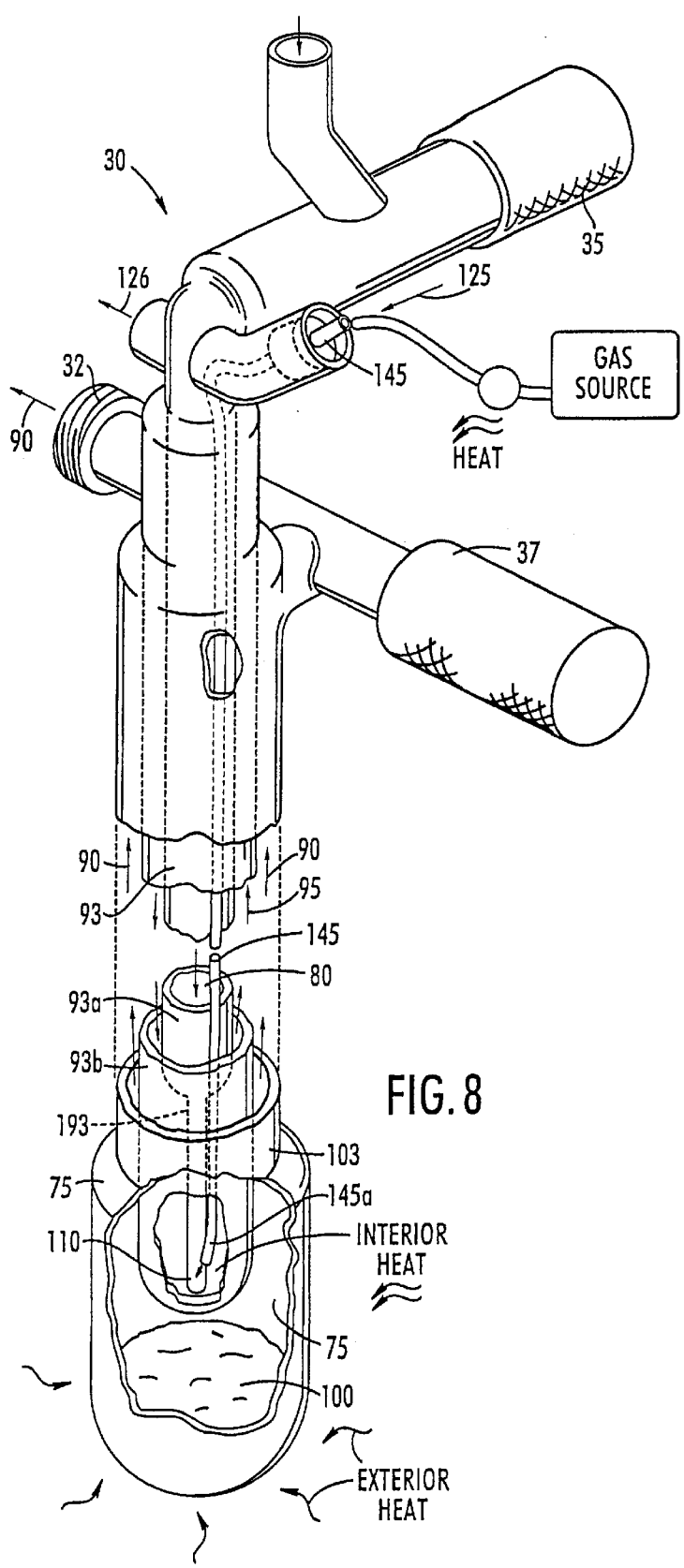
FIG. 8 illustrates the accumulator of FIG. 7 with heat applied during a thawing process according to one embodiment of the present invention.

Advantageously, the heating jacket 93 of the accumulator 30, 30' described above can additionally improve the thawing process. Turning to FIG. 8, the heating jacket or secondary flow channel 95 of the accumulator can supply heat to the nozzle area 110 of the accumulator 30 during the thawing process. Preferably the lower area of the flow path or the nozzle area is preheated before thawing so that the nozzle 110 is well above the freezing point of the polarized gas prior to applying heat to the external surface of the reservoir 75. It is additionally preferred, that during the thawing, heat is supplied to both the exterior and the interior of the cold finger. The interior heating being preferably applied to the lower region of the accumulator, i.e., the nozzle area. The nozzle 110 is thus warmed by the circulating fluid (preferably gas) in the heating jacket 93. Various warming gases such as those described above can be used.

Preferably, the flow rate of the warming gas is higher than that used during the accumulation process, such as about 39.329–94.39 ml/s (5–12 ft$^3$/hr), and more preferably at about 78.658 ml/s (10 ft$^3$/hr) during thaw. Similarly, the preferred temperatures of the "warming" gas supplied during thawing are at typical internally controlled ambient conditions (for example room temperature gases such as 20–25.6° C. (68–78° F.)).

For a "transported" accumulator 30, once all the $^{129}$Xe is liquid, the isolation valve 35 is preferably opened leading to an attached evacuated chamber or bag or other delivery means or collection vessel. Of course either of the valves 35, 37 can be opened depending on where the delivery vessel or receptacle is attached (not shown). For the "on-board" accumulator, isolation valve 37 is the operative valve as described above. The sudden decrease in pressure causes the liquid $^{129}$Xe to become gaseous and exit the accumulator 30 rapidly, advantageously thereby spending a minimum amount of time in the inhomogeneous magnetic field in the gaseous state. Similarly, if the "on-board" release is employed, the isolation valve 37 is opened and the gas flows through valve 47 and exits outlet 50 into a delivery vessel. Conventional methods of thawing included opening the cold finger (accumulator) to the vessel to be filled and then starting the thaw. This thaw could typically take 30 seconds or more to complete for single patient dose amounts. In comparison and advantageously, the instant thaw method can be completed in less than about 10 seconds, and preferably in less than about 5–6 seconds for single dose amounts of frozen hyperpolarized gas. A typical patient dose is from about 0.20–1.25 liters ("L") and preferably about 0.5–1.0 L. The conversion weight is about 5.4 grams/L of Xe. Similarly, the density of solid Xe is about 3.1 g/cm$^3$, and a corresponding patient volume of polarized frozen Xe can be calculated at about 1.8 cm$^3$/L.

Advantageously, observations of the instant thawing method indicate a reliable factor of about 2 or more improvement in the final polarization level of thawed $^{129}$Xe as compared to that thawed by conventional methods.

Figure 12A:
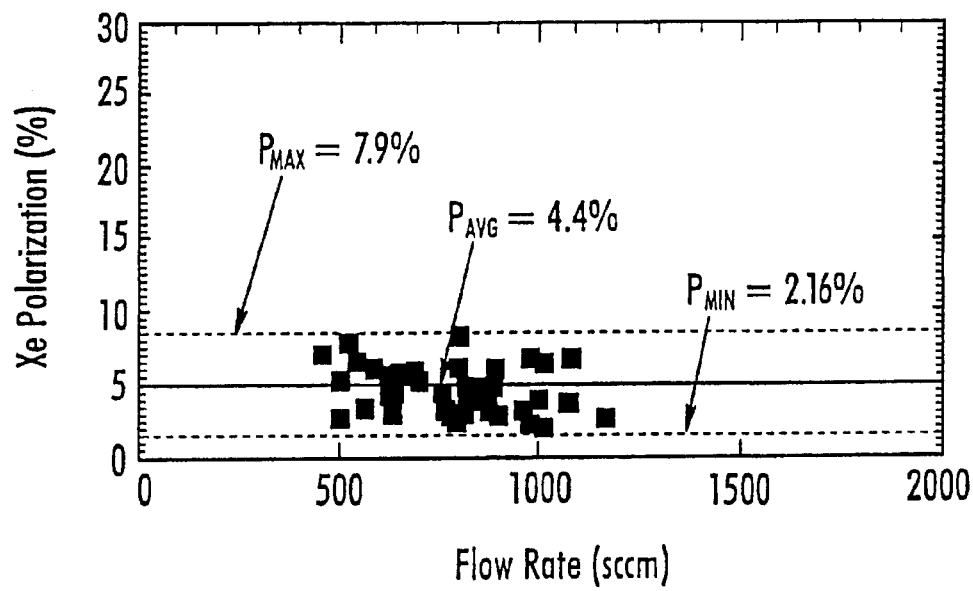
FIG. 12A graphically illustrates polarization levels after thaw versus accumulation flow rates of a polarized gas thawed using a conventional thaw method.
Figure 12B:
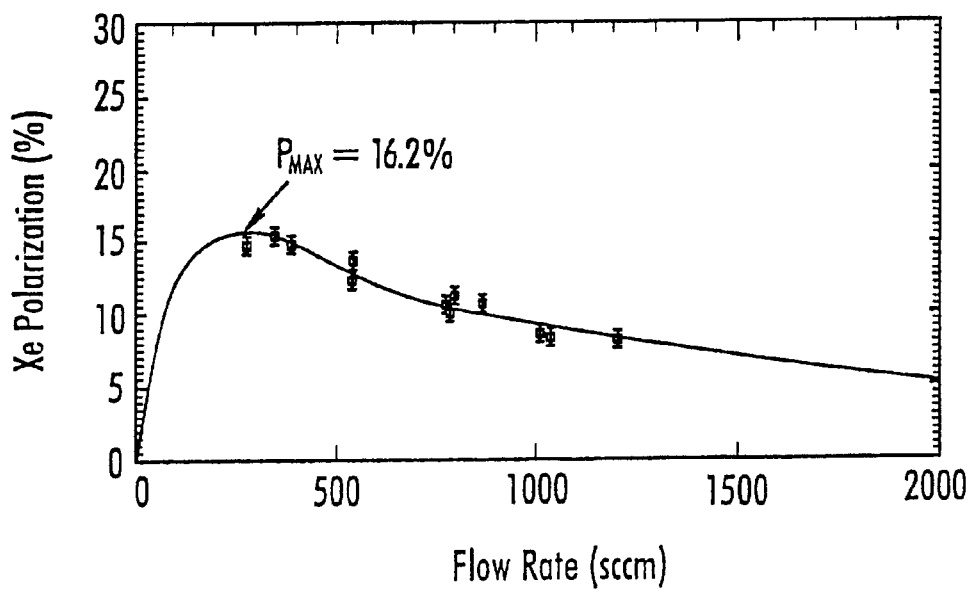
FIG. 12B graphically illustrates exemplary polarization levels after thaw versus accumulation flow rates of a polarized gas thawed according to the present invention.

Referring now to FIGS. 12A and 12B, FIG. 12A illustrates the polarization results obtained by a conventional thaw technique while FIG. 12B graphically illustrates results obtained by the improved thaw method of the instant invention as described above. Each of the graphs plot % polarization of $^{129}$Xe after thaw in relationship to the total gas flow rate through the polarization cell 22 (and therefore the entire unit). The corresponding $^{129}$Xe flow rate is the % of the total gas mix. In the example shown, $^{129}$Xe makes up about 1% of the total gas mix, thus the $^{129}$Xe-flow rate is the total flow rate divided by 100. For example at a flow rate of 1000 standard cm$^3$ (standard cubic centimeters per minute ("sccm")), $^{129}$Xe is typically accumulated at the rate of 10 cm$^3$ per min or 600 cm$^3$ per hour. Higher flow rates are desired to increase the through-put of $^{129}$Xe. However, polarization is reduced at higher flow rates. This is attributed to the reduced time that the $^{129}$Xe spends in residence time in spin exchange contact with the optically pumped Rb at higher flow rates. That is, the Xe residence time in the cell 22 can generally be described mathematically as equal to the gas pressure multiplied by the cell volume divided by the flow rate (PV/m).

FIG. 12A shows the conventional thaw technique yields scattered polarization results which are attributed to random polarization losses mainly occurring during thawing. FIG. 12B tracks with the optical pumping characteristics described above and now produces predictable post-thaw polarization levels corresponding to the accumulation flow rate.

As shown in FIG. 12B, when thawing according to the improved method described above (under pressurization and with internal and external heating), for flow rates below 1000 sccm (or standard cm³/min), polarization levels after thaw of above 10% are reliably achieved. The results shown in this figure represent a 190 cm³ volume of $^{129}$Xe (and Rb polarization levels of about 0.25–0.49). Of course, as will be appreciated by one of skill in the art, different volumes (i.e., larger or smaller) of the polarized gas will have different relative values associated therewith. For example, larger volumes of $^{129}$Xe takes longer times to polarize, therefore at the same flow rates, the polarization of the larger volume will be less than that shown in FIG. 12B. Stated differently, for larger amounts of polarized gas, the associated polarization curve will drop below the values shown relative to that for an exemplary 190 cm³ volume of polarized gas as shown in FIG. 12B. Also, typically, larger amounts of polarized gas can result in a larger loss attributed to solid-phase relaxation. However, as shown by the graph, the instant invention now provides a frozen gas thaw method which results in a post-thaw polarization curve which predictably follows the initial polarization curve. In contrast, as shown by FIG. 12A, the conventional polarization level after thaw is highly unpredictable, with an average of about 4.4%. Indeed, at about 900 sccm (standard cm³/min), the polarization point is about 2.16% while prediction is 18.7%, thus making the retention fraction a low 12.2% (losing about 87.8% of the starting polarization). Unlike the conventional method, the instant invention produces polarization levels after thaw that predictably corresponds to the flow rate used during accumulation.

FIG. 13 illustrates experimental and theoretical polarization levels before and after thawing. The experimental flowing curve shows the polarization levels achieved before freezing (the level measured as the $^{129}$Xe exits the pumping cell 22). The experimental data points on the graph represent thawed data points achieved by thawing the collected, frozen polarized gas according to the present invention. The experimental data confirms that the methods of the instant invention improve the predictability of the polarization retention fraction now achievable as well as increases the value of the polarization retention fraction (amount of polarization retained post-thaw relative to that attained prior to freeze).

FIG. 13A illustrates a flow curve used to predict polarization levels as expected from a thawed polarized xenon product, this curve representing post-thaw polarization levels achievable absent polarization losses during freezing and thawing. This curve includes losses from normal relaxation of solid Xe (which can be generally estimated to be approximately 2 hours at 77° K). As shown, low flow rates typically have an associated relatively large polarization loss. This is because, at low flow rates, the accumulation time can be extensive and the ice "T1" then plays a larger or more dominant role. As shown, the polarization retention fraction achieved using the freezing and thawing methods of the instant invention is above 40% for all flow rates, and the average is about 49.9%. Therefore, as shown in FIG. 13A, this polarization retention fraction is substantially insensitive to flow rate. The below listed data shows exemplary polarization retention fractions now achievable.

| Flow Rate | Polarization (P)$_{theory}$ | P$_{exper.}$ | Retention Fraction |
|---|---|---|---|
| 300 | 24 | 12.66 | 52.8% |
| 600 | 22.1 | 11.18 | 50.6% |
| 900 | 18.7 | 9.30 | 49.7% |
| 1200 | 15.9 | 7.83 | 49.2% |
| 1500 | 13.75 | 6.73 | 48.9% |
| 1800 | 12.08 | 5.90 | 48.8% |
| 2000 | 11.1 | 5.43 | 48.9% |

For example, a data point at a flow rate of 600 sccm has a theoretical polarization level of 22.1 and a corresponding experimental data point of 11.18 polarization after thaw. The initial polarization level (before- accumulation/freezing) for this flow rate is 22.1%. Therefore, the polarization retention fraction after the freeze/thaw process is 11.18/22.1 or 50.6%. Thus, advantageously, the instant thawing technique retains at least 30% of the initial polarization level and based on this data preferably above 40% of the initial polarization level, and most preferably above 45%. Further the improved retention rate increases the thawed polarization level by an order of magnitude (now reliably and predictably above about 10% in contrast to conventional thawed polarization levels of about 2%).

Although particularly suited for $^{129}$Xe, the instant thawing method can also successfully be employed with other hyperpolarized noble gases. Further, it will be appreciated by those of skill in the art, that the cryogen used to freeze the polarized gas is not limited to liquid $N_2$. However, if alternate refrigeration sources or cryogens are used then flow rates, accumulation rates, "warming" gas temperatures and the like should be adjusted accordingly. Further, it is desired to use refrigeration sources with temperatures at least as low as liquid nitrogen (77K) for collection of the polarized gas. Lower temperatures increase the T1 time of the solid polarized gas which results in increased relaxation times. For example, polarized gases frozen at liquid nitrogen temperatures have an ice relaxation time (T1) of approximately 2.8 hours while polarized gases frozen at liquid helium temperatures have an ice relaxation time (T1) of approximately 12 days. Therefore, in order to achieve higher polarization levels after thawing, the thawing is preferably performed within the corresponding T1 time period.

Figure 9:
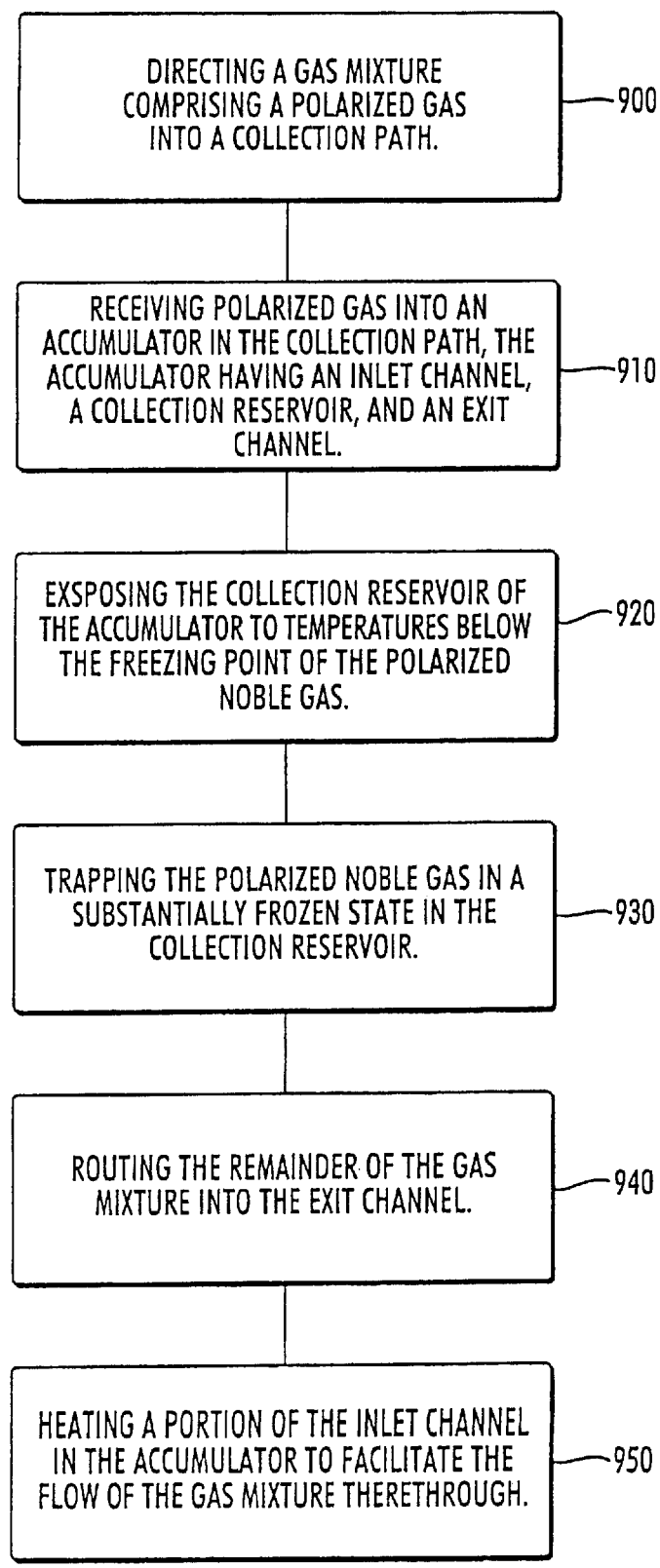
FIG. 9 is a block diagram illustrating the steps of a method for accumulating polarized gas according to the present invention.
Figure 10:
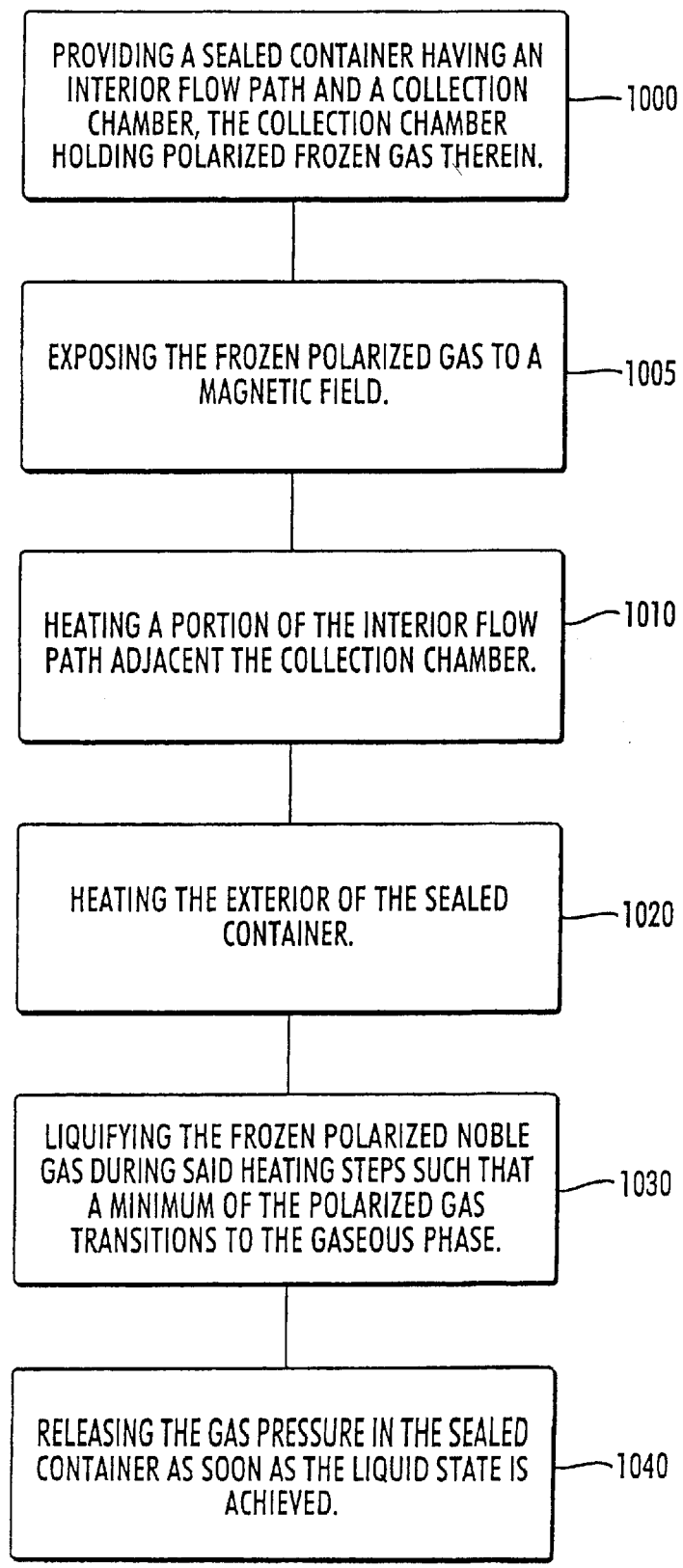
FIG. 10 is a block diagram illustrating the steps of a method for thawing frozen polarized gas according to one embodiment of the present invention.
Figure 11:
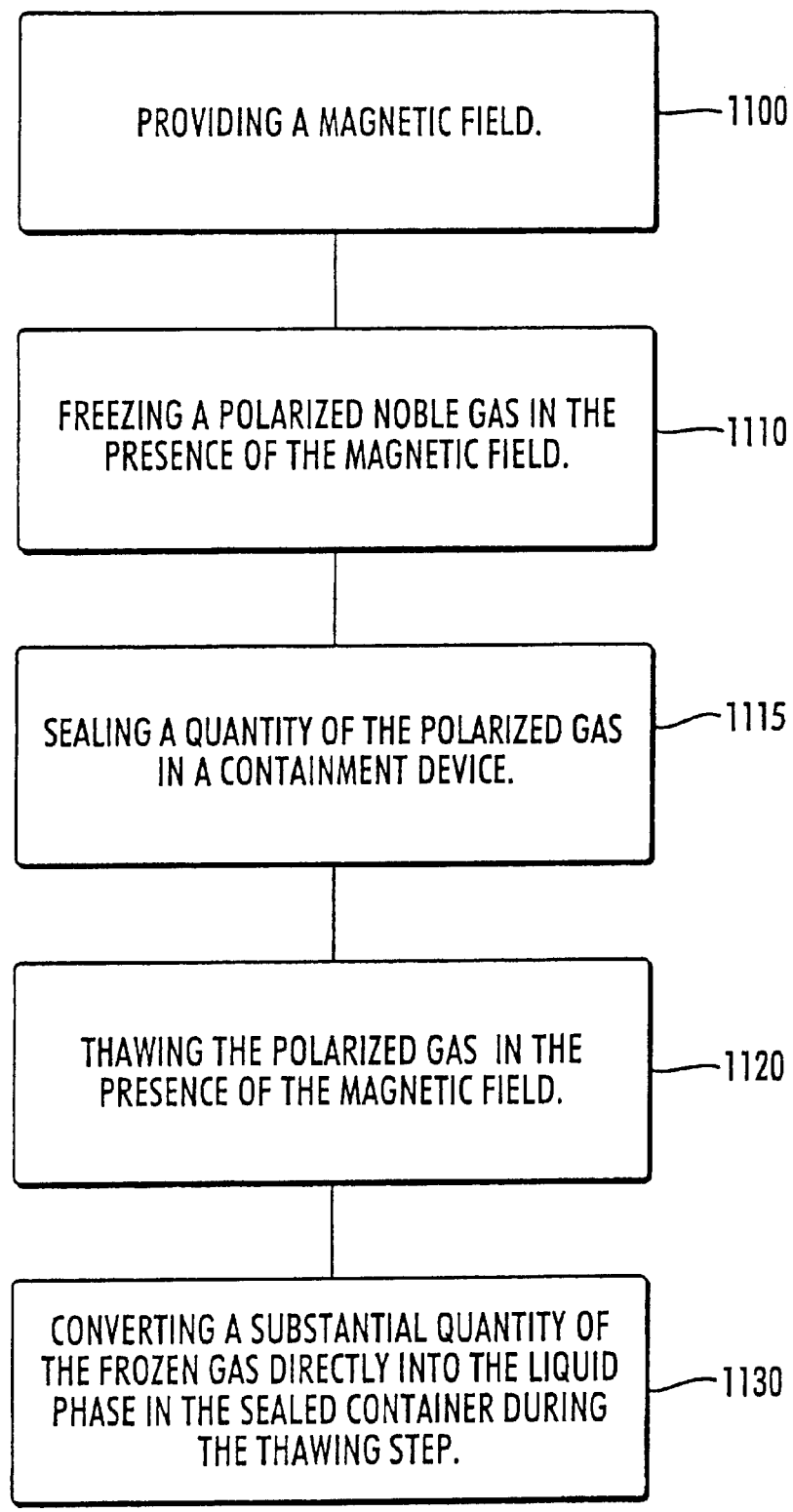
FIG. 11 is a block diagram illustrating the steps of a method for extending the useful life of a polarized gas according to one embodiment of the present invention.

FIGS. 9, 10, and 11 are block diagrams of methods associated with the instant invention. The order of the methods is not meant to be limited by the block numbers and order shown. Additional steps can also be included as operationally described hereinabove.

FIG. 9 shows steps for accumulating or collecting frozen polarized gas according to one embodiment of the instant invention A gas mixture comprising a polarized gas is directed into collection path (Block 900). The polarized gas is received into the accumulator in the collection path. The accumulator has an inlet channel, a collection reservoir, and an exit channel (Block 910). The collection reservoir is exposed to temperatures below the freezing point of the polarized noble gas (Block 920). The polarized gas is trapped in a substantially frozen state in the collection reservoir (preferably a total solid frozen state)(Block 930). The remainder of the gas mixture is routed into the exit channel (Block 940). A portion of the inlet channel in the accumulator is heated to facilitate the flow of the gas mixture therethrough (Block 950). The heating step (Block 950) is preferably carried out by introducing a gas separate from the gas mixture to conductively heat a predetermined area of the inlet channel, the separate gas being contained apart from the inlet and exit paths. The contained separate gas is then circulated about a portion of the inlet path to reduce the likelihood of blockage along the inlet path attributed to the exposing step.

FIG. 10 illustrates a method for thawing frozen polarized gas according to a preferred embodiment of the present invention. A sealed container is provided which includes an interior flow path and a collection chamber for holding frozen polarized gas (Block 1000). The frozen gas is exposed to a magnetic field (Block 1005). A portion of the interior flow path adjacent the collection chamber is heated (Block 1010). The exterior of the sealed container is also heated (Block 1020). The frozen gas is liquefied during the heating steps such that a minimum amount of the polarized gas transitions to the gaseous phase (and conversely, a substantial amount of the polarized gas transitions directly to the liquid phase) (Block 1030). Preferably, the liquefying step is carried out by closing the isolation valves and sealing the container allowing the pressure to build to a predetermined level, the level corresponding to the time it takes to provide an "instantaneous" thaw. Stated differently, the valves remain closed for as short a period as possible (as described above, less than about 10 seconds for a single patient dose), the period corresponding to the time it takes to achieve substantially full gas pressure upon opening the accumulator isolation valve. The release pressure can be calculated according to a liquid Xe vapor pressure curve. See V. A. Rabinovich et al., *Thermophysical Properties of Neon, Argon, Krypton, and Xenon* (Hemisphere Publishing Corp., Wash, 1988). An exemplary pressure release is thought to be less than approximately 506.625–1013.25 kPa (5–10 atm) (and at least less than about 1722.525 kPa (17 atm)) for a 0.5 L accumulation in a 30 cm$^3$ accumulator at a temperature below 200 K. This value will be different for different cold finger volumes, different accumulation volumes, and the temperature of the gas in liquid Xe. The Sauer et al. reference, supra, indicates that for Xe at 161.4 K, P=81.06 kPa (0.81 atm), and the triple point 289.7 K, P=5775.525 kPa (57 atm), and at 240 K, P=4053 kPa(40 atm). Thus, as indicated by Block 1040, the gas pressure is released from the sealed container as soon as the liquid state is achieved. It is also preferred that the interior be heated as described above.

FIG. 11 illustrates a method for extending the useful polarization life of a polarized gas product according to one embodiment of the present invention. A magnetic field is provided (Block 1100). The polarized gas product is frozen in the presence of the magnetic field (Block 1110). A quantity of the frozen polarized gas is sealed in a containment device (Block 1115). The polarized gas is thawed in the presence of a magnetic field (Block 1120). A substantial quantity of the frozen gas is converted directly into the liquid phase in the sealed container during the thawing step (Block 1130). Although not shown in this figure, various other steps can be employed along the lines described hereinabove. (For example, other steps can include, but are not limited to, decreasing the amount of $^{131}$Xe in the enriched gas mixture, heating the interior of the flow path, using a nozzle to direct the flow of gas, depressurizing the containment device by opening the valves causing the liquid to become gas and releasing the polarized gas to a interface such as a bag or other delivery device).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A cryogenic accumulator for collecting polarized noble gases in a buffer gas mixture, comprising:
   a primary flow channel having opposing first and second ends configured to direct a gas mixture comprising polarized gas therethrough, said primary flow channel having an inlet flow path and an exit flow path associated therewith;
   an outer sleeve positioned around said primary flow channel, said outer sleeve having a closed end defining a collection chamber positioned below said primary flow channel second end; and
   a secondary flow channel positioned intermediate of said primary flow channel and said outer sleeve, said secondary flow channel having a fluid inlet and outlet region associated therewith, said secondary flow channel having a closed end positioned in close proximity to said primary flow channel second end, wherein said secondary flow channel is operably associated with said primary flow channel,
   wherein said primary flow channel inlet flow path is in fluid communication with and separate from said primary flow channel exit flow path, and wherein said primary flow channel inlet flow path terminates into said collection chamber and said exit flow path originates proximate said collection chamber so that, in operation, the polarized gas mixture travels first through said inlet flow path, then into said collection chamber such that residual gases from the polarized gas mixture are directed out of said chamber and into said exit flow path.

2. A cryogenic accumulator according to claim 1, said secondary flow channel having a cylindrically shaped inner wall, wherein said secondary flow channel inner wall defines said primary flow channel.

3. A cryogenic accumulator according to claim 2, said secondary flow channel having an outer wall, wherein said outer wall and said outer sleeve define said primary flow channel exit flow path therebetween.

4. A cryogenic accumulator according to claim 2, further comprising first and second isolation valves in fluid communication with said primary flow channel inlet flow path and said primary flow channel exit flow path.

5. A cryogenic accumulator according to claim 4, wherein said second isolation valve is positioned spaced-apart from said accumulator outer sleeve closed end along said primary flow channel exit flow path to releasably seal and control the release of gas therethrough.

6. A cryogenic accumulator according to claim 2, wherein said secondary flow channel includes a longitudinally extending conduit configured to direct a gas to said secondary flow channel closed end adjacent said second end of said primary flow channel.

7. A cryogenic accumulator according to claim 1, wherein said primary flow channel second end is a nozzle having a reduced cross-sectional size relative to said primary flow channel above said nozzle.

8. A cryogenic accumulator according to claim 7, wherein said first isolation valve is positioned at said first end of said primary flow channel to control the flow of the gas mixture gas therethrough.

9. A cryogenic accumulator according to claim 1, wherein said secondary flow channel fluid inlet region comprises an inlet port and said outlet region comprises a vent port, and a conduit in fluid communication with said inlet port, wherein said conduit extends along a major portion of said secondary flow channel to thereby direct the flow of a warming gas to a predetermined region of said primary flow channel.

10. A cryogenic accumulator according to claim 1, in combination with a hyperpolarizer unit, wherein said accumulator is configured to detachably release from said hyperpolarizer unit.

11. A cryogenic accumulator according to claim 1, wherein said secondary flow channel is in fluid isolation from said primary flow channel.

12. A cryogenic accumulator according to claim 11, wherein said secondary flow channel is configured, in operation, as a heat source which is operably associated with said primary flow channel.

13. A cryogenic accumulator according to claim 12, further comprising at least one permanent field magnet positioned adjacent said collection chamber.

14. A cryogenic accumulator according to claim 11, wherein said secondary flow channel is an enclosed heating jacket configured, in operation, to circulate gas therethrough proximate said primary flow channel.

15. A cryogenic accumulator according to claim 14, further comprising a cryogenic refrigeration source operably associated with said collection chamber.

16. A cryogenic accumulator according to claim 14, wherein said secondary flow channel is configured to circulate ambient temperature gaseous nitrogen therethrough.

17. A cryogenic accumulator according to claim 14, wherein said secondary flow channel outlet region includes at least one secondary flow channel vent port in fluid communication with said secondary flow channel.

18. A cryogenic accumulator according to claim 17, further comprising a flow adjustment valve operably associated with said vent to adjust the flow of a gas in said secondary flow channel thereby adjusting the heat supplied to at least a portion of said primary flow channel.

19. A cryogenic accumulator according to claim 1, wherein said outer sleeve, said secondary flow channel, and said primary flow channel inlet and exit paths are radially aligned along a major portion of the length of said accumulator.

20. A heating jacket for a refrigerated accumulator, comprising:

an outer wall having opposing first and second ends;

an inner wall having opposing first and second ends, said inner wall being spaced apart from said outer wall, wherein said inner wall is configured to be in close proximity to a polarized gas collection path;

a bottom sealed to each of said outer and inner wall second ends;

a top sealed to each of said outer and inner wall first ends, wherein said top, bottom, and inner and outer walls define at least one enclosed fluid circulation channel therebetween;

a fluid inlet in communication with said circulation channel;

a fluid vent configured in communication with said circulation channel;

a heat source comprising a gas, wherein said fluid inlet and vent are configured to allow flow of the gas in said circulation channel.

21. A heating jacket according to claim 20, wherein said fluid inlet is operably associated with a valve, and wherein said valve provides an adjustable flow rate of the gas in said circulation channel.

22. A heating jacket according to claim 21, wherein said inner wall includes a first portion defining a flow channel first diameter, and a stepped down second portion defining a flow channel second diameter, said second diameter being smaller than said first diameter.

23. A heating jacket according to claim 22, wherein said stepped down portion defines a flow channel nozzle.

24. A heating jacket according to claim 20, wherein said inner and outer walls are substantially cylindrical and radially aligned.

25. A heating jacket according to claim 20, said inner wall circumferentially extends around a center opening to define a flow channel therethrough for a polarized gas.

26. A heating jacket according to claim 20, further comprising an elongated conduit positioned in said enclosed circulation channel and operably associated with said fluid inlet.

27. An accumulator for collecting a polarized gas, comprising:

a primary flow channel having opposing inlet and exit ends, said exit end configured as a flow nozzle, wherein said flow nozzle is defined by a reduced cross-sectional size along said exit end of said primary flow channel relative to said primary flow channel cross-sectional size upstream thereof, and wherein said inlet end is detachably connected to a polarized gas collection path; and an outer sleeve including a collection reservoir aligned with and positioned adjacent to said flow nozzle.

28. An accumulator according to claim 27, further comprising a heat source positioned intermediate of said primary flow channel and said outer sleeve before said collection chamber, said heat source arranged to provide heat to said flow nozzle.

29. An accumulator for collecting a polarized gas, comprising:

a primary flow channel having opposing inlet and exit ends, said exit end configured as a flow nozzle, wherein said inlet end is detachably connected to a polarized gas collection path;

an outer sleeve including a collection reservoir aligned with and positioned adjacent to said flow nozzle; and a heat source positioned intermediate of said primary flow channel and said outer sleeve before said collection chamber, said heat source arranged to provide heat to said flow nozzle, wherein said heat source comprises an enclosed heating jacket positioned inside of and spaced-apart from said outer sleeve.

30. An accumulator according to claim 29, wherein said enclosed heating jacket includes a circumferentially extending inner wall which defines said primary flow channel.

31. An accumulator according to claim 30, wherein said enclosed heating jacket includes a circumferentially extending outer wall spaced-apart from said inner wall which together with said outer sleeve defines an exit path in communication with said primary flow path.

32. An accumulator according to claim 30, wherein said enclosed heating jacket includes a vent port, and wherein said heating jacket is configured to circulate gas to conductively heat said inner wall and capture the gas and return it to said vent port.

33. An accumulator for collecting a polarized gas, comprising:
- a primary flow channel having opposing inlet and exit ends, said exit end configured as a flow nozzle, wherein said inlet end is detachably connected to a polarized gas collection path;
- an outer sleeve including a collection reservoir aligned with and positioned adjacent to said flow nozzle; and
- a heat source positioned intermediate of said primary flow channel and said outer sleeve before said collection chamber, said heat source arranged to provide heat to said flow nozzle, wherein said heat source includes a conduit for directing a flow of a predetermined gas to said flow nozzle.

34. A cryogenic accumulator container with a heating jacket configured to direct warming fluid proximate to but separate from flowable polarized gas mixtures during operation when the cryogenic accumulator container is exposed to a cooling source so as to facilitate the accumulation of polarized gas in a substantially frozen state therein, comprising:
- a polarized gas flow channel having a downwardly extending flow inlet path ending into a closed end collection segment at a bottom portion of said accumulator container and an exhaust path separate from said flow inlet path, wherein in operation, said exhaust path is configured to direct residual gases separated from the polarized gas mixture out of said accumulator container and upwardly away from said closed end collection segment, said exhaust path being positioned separate from said flow inlet path and proximate to an outer perimeter of said accumulator container; and
- a secondary fluid flow channel positioned intermediate said flow inlet path and said exhaust path such that it extends proximate to at least a portion of the length of said polarized gas flow inlet path above said closed end collection segment, wherein said secondary fluid flow channel is in fluid isolation of said polarized gas flow inlet path and configured to heat a portion of said polarized gas flow channel inlet path above said collection segment.

35. A cryogenic accumulator container with a heating jacket according to claim 34, wherein said polarized gas flow channel inlet path is substantially centrally positioned within said accumulator container, and wherein said secondary fluid flow channel includes first and second downwardly extending walls defining an enclosed space therebetwen, and wherein said first and second walls extend between said inlet and exhaust paths to thereby separate said inlet and exhaust paths.

36. A cryogenic accumulator container with a heating jacket according to claim 35, wherein downward end portions said first and second walls are configured to define a nozzle segment along said inlet path above said closed end of said collection segment of said accumulator container.

37. A cryogenic accumulator container with a heating jacket according to claim 35, further comprising a quantity of a polarized gas mixture, and wherein said polarized gas mixture comprises a polarized noble gas having an associated freezing point, and wherein said secondary fluid flow channel is configured to circulate fluid therein at a temperature above the freezing point of the polarized gas in said polarized gas mixture.

38. A cryogenic accumulator container with a heating jacket according to claim 37, wherein said polarized gas mixture comprises $^{129}Xe$.

39. A cryogenic accumulator container with a heating jacket according to claim 38, wherein said secondary fluid flow channel is configured to circulate a gas therein at a temperature above 160° K.

40. A cryogenic accumulator container with a heating jacket according to claim 35, further comprising a fluid inlet port and a spaced apart fluid outlet port in fluid communication with said secondary flow channel, and a flowable warming gas source configured to direct warming gas into said fluid inlet port of said secondary flow channel at a desired rate.

41. A cryogenic accumulator container with a heating jacket according to claim 40, wherein said warming gas flow rate is between about 1–6 ft$^3$/hr.

42. A cryogenic accumulator container with a heating jacket according to claim 41, wherein said warming gas has a temperature of between about 50–80° F.

43. A cryogenic accumulator container with a heating jacket according to claim 42, wherein said warming gas comprises nitrogen.

44. A cryogenic accumulator container with a heating jacket according to claim 34, wherein said cryogenic accumulator container is operably associated with a polarizer unit configured to optically polarize a noble gas through alkali metal spin-exchange, and wherein said cryogenic accumulator comprises at least one valve in fluid communication with said polarized gas flow channel inlet flow path such that said accumulator container is sealably detachable from said optical polarizer unit after a desired quantity of polarized gas has been substantially solidified and thereby collected therein.

* * * * *

UNITED STATES PATENT AND TRADEMARK OFFICE
CERTIFICATE OF CORRECTION

PATENT NO.    : 6,199,385 B1
DATED         : March 13, 2001
INVENTOR(S)   : Driehuys et al.

Page 1 of 1

It is certified that error appears in the above-identified patent and that said Letters Patent is hereby corrected as shown below:

<u>Title page,</u>
Item [56], under "OTHER PUBLICATIONS", the Borman reference should read as follows -- Borman, Xenon used to expand magnetic imaging, Chem. & Eng. News, vol. 72, No. 30, pp. 7-8 (Jul. 25, 1994). -- and
The Zeng et al. reference should read -- Zeng et al., "Experimental determination of the rate constants for spin exchange between optically pumped K, Rb, and Cs atoms and $^{129}$Xe nuclei in alkali-metal-noble-gas van der Waals molecules", *Physical Review A*, vol. 31, p. 260 (1985). --

Signed and Sealed this

Second Day of April, 2002

Attest:

Attesting Officer

JAMES E. ROGAN
*Director of the United States Patent and Trademark Office*